United States Patent
Sitton

(10) Patent No.: US 12,379,379 B2
(45) Date of Patent: Aug. 5, 2025

(54) ASSAY

(71) Applicant: NEOGEN FOOD SAFETY US HOLDCO CORPORATION, Lansing, MI (US)

(72) Inventor: Gregory W. Sitton, Minneapolis, MN (US)

(73) Assignee: NEOGEN FOOD SAFETY US HOLDCO CORPORATION, Lansing, MI (US)

( * ) Notice: Subject to any disclaimer, the term of this patent is extended or adjusted under 35 U.S.C. 154(b) by 933 days.

(21) Appl. No.: 17/258,576

(22) PCT Filed: Jul. 10, 2019

(86) PCT No.: PCT/IB2019/055896
§ 371 (c)(1),
(2) Date: Jan. 7, 2021

(87) PCT Pub. No.: WO2020/012391
PCT Pub. Date: Jan. 16, 2020

(65) Prior Publication Data
US 2021/0270838 A1    Sep. 2, 2021

Related U.S. Application Data

(60) Provisional application No. 62/697,514, filed on Jul. 13, 2018.

(51) Int. Cl.
| | |
|---|---|
| B01L 3/00 | (2006.01) |
| A61B 6/00 | (2024.01) |
| A61B 8/00 | (2006.01) |
| B01F 23/00 | (2022.01) |
| B01F 23/41 | (2022.01) |
| B01F 101/23 | (2022.01) |
| B23Q 17/24 | (2006.01) |
| C07K 14/705 | (2006.01) |
| C12M 1/34 | (2006.01) |
| C12Q 1/04 | (2006.01) |
| C12Q 1/18 | (2006.01) |
| C12Q 1/686 | (2018.01) |
| G01N 1/31 | (2006.01) |
| G01N 15/10 | (2024.01) |
| G01N 21/3577 | (2014.01) |
| G01N 21/359 | (2014.01) |
| G01N 21/39 | (2006.01) |
| G01N 21/45 | (2006.01) |
| G01N 21/64 | (2006.01) |
| G01N 21/77 | (2006.01) |
| G01N 21/78 | (2006.01) |
| G01N 27/414 | (2006.01) |
| G01N 27/62 | (2021.01) |
| G01N 30/12 | (2006.01) |
| G01N 30/68 | (2006.01) |
| G01N 30/70 | (2006.01) |
| G01N 30/72 | (2006.01) |
| G01N 30/88 | (2006.01) |
| G01N 33/00 | (2006.01) |
| G01N 33/18 | (2006.01) |
| G01N 33/50 | (2006.01) |
| G01N 33/53 | (2006.01) |
| G01N 33/542 | (2006.01) |
| G01N 33/543 | (2006.01) |
| G01N 33/58 | (2006.01) |
| G01N 33/68 | (2006.01) |
| G01N 33/74 | (2006.01) |
| G01N 35/00 | (2006.01) |
| G01N 35/10 | (2006.01) |
| G06K 7/10 | (2006.01) |
| G06K 7/14 | (2006.01) |
| G06K 19/06 | (2006.01) |
| G06K 19/07 | (2006.01) |
| G06T 7/00 | (2017.01) |
| G06T 7/90 | (2017.01) |
| G16H 10/40 | (2018.01) |

(Continued)

(52) U.S. Cl.
CPC ......... G01N 33/582 (2013.01); G01N 33/542 (2013.01); G01N 33/581 (2013.01)

(58) Field of Classification Search
CPC .. G01N 33/582; G01N 33/542; G01N 33/581; C12Q 1/28
See application file for complete search history.

(56) References Cited

U.S. PATENT DOCUMENTS

| 4,837,395 A | 6/1989 | Leeder |
| 5,089,383 A | 2/1992 | Leeder |

(Continued)

FOREIGN PATENT DOCUMENTS

| JP | 61264262 | 1/1986 |
| JP | 2002524102 | 8/2002 |

(Continued)

OTHER PUBLICATIONS

"Custom Acridan Conjugation Of Antibodies For Use In SPARCL™ Assays", Acridan Conjugation Service, Life Diagnostics, Inc., 2017, p. 1.

(Continued)

*Primary Examiner* — Jennifer Wecker
*Assistant Examiner* — Oyeleye Alexander Alabi
(74) *Attorney, Agent, or Firm* — HYLTON-RODIC LAW PLLC

(57) ABSTRACT

Method of assaying for an analyte in a sample, and kits for performing the assay.

5 Claims, No Drawings

(51) Int. Cl.
    *G16H 10/60*    (2018.01)
    *G16H 30/40*    (2018.01)
    *G16H 50/20*    (2018.01)
    *G16H 80/00*    (2018.01)
    *H01J 49/00*    (2006.01)
    *H04M 17/00*    (2024.01)
    *H10K 10/46*    (2023.01)
    *H10K 85/00*    (2023.01)
    *H10K 85/20*    (2023.01)

(56) References Cited

U.S. PATENT DOCUMENTS

| | | | |
|---|---|---|---|
| 5,171,668 | A | 12/1992 | Sugiyama |
| 5,206,149 | A | 4/1993 | Oyama |
| 5,324,835 | A | 6/1994 | Yamaguchi |
| 5,420,275 | A | 5/1995 | Masuya |
| 5,491,072 | A | 2/1996 | Akhavan-Tafti |
| 5,497,072 | A | 3/1996 | LeComte |
| 5,512,451 | A | 4/1996 | Kricka |
| 5,523,212 | A | 6/1996 | Akhavan-Tafti |
| 5,593,845 | A | 1/1997 | Akhavan-Tafti |
| 5,922,558 | A | 7/1999 | Akhavan-Tafti |
| 6,030,803 | A | 2/2000 | Jacquemijns |
| 6,162,610 | A | 12/2000 | Bronstein |
| 6,406,913 | B1 | 6/2002 | Ullman |
| 6,696,569 | B2 | 2/2004 | Akhavan-Tafti |
| 6,891,057 | B2 | 5/2005 | Akhavan-Tafti |
| 6,911,305 | B2 | 6/2005 | Levison |
| 7,732,153 | B2 | 6/2010 | Akhavan-Tafti |
| 9,029,092 | B2 | 5/2015 | Akhavan-Tafti |
| 2006/0046302 | A1 | 3/2006 | Springston |
| 2007/0172878 | A1 | 7/2007 | Akhavan-Tafti |
| 2007/0264664 | A1* | 11/2007 | Akhavan-Tafti ............................ G01N 33/54306 435/7.93 |
| 2007/0264665 | A1 | 11/2007 | Akhavan-Tafti |
| 2010/0267071 | A1 | 10/2010 | Akhavan-Tafti |
| 2013/0084652 | A1 | 4/2013 | Shapir |
| 2015/0212005 | A1* | 7/2015 | Akhavan-Tafti ......... C12Q 1/28 435/7.9 |

FOREIGN PATENT DOCUMENTS

| | | |
|---|---|---|
| WO | WO 1991-019979 | 12/1991 |
| WO | WO 2000-015618 | 3/2000 |
| WO | WO 2007-058654 | 5/2007 |
| WO | WO 2007-133988 | 11/2007 |
| WO | WO 2007-134098 | 11/2007 |
| WO | WO 2010-099486 | 9/2010 |

OTHER PUBLICATIONS

"Homogeneous Immunoassay", Lumigen SPARCL, [retrieved from the internet on Feb. 28, 2021], URL <http://www.lumigen.com/products/elisa/lumigen-sparcl>, 2021, pp.

Akhavan-Tafti, "A Homogeneous Chemiluminescent Immunoassay Method", Journal of The American Chemical Society, 2013, vol. 135, No. 11, pp. 4191-4194.

Ci, "The Use of Mn-TPPS$_4$ Mimetic Peroxidase in a DNA Hybridization Assay", Microchemical Journal, 1995, vol. 52, pp. 257-262.

Ji, "Bifunctional Reagents", Methods in Enzymology, 1983, vol. 91, pp. 580-609.

Martinello, "Mechanism Of Ascorbic Acid Interference In Biochemical Tests That Use Peroxide And Peroxidase To Generate Chromophore", Clinica Chimica Acta, 2006, vol. 373, pp. 108-116.

Tyrrell, "Development Of A Micro-Fluidic Manifold For Copper Monitoring Utilizing Chemiluminescence Detection", The Royal Society of Chemistry, Lab Chip, 2004, vol. 04, pp. 384-390.

Velijovic-Jovanovic, "Are Leaf Hydrogen Peroxide Concentrations Commonly Overestimated? The Potential Influence Of Artefactual Interference By Tissue Phenolics And Ascorbate", Plant Physiology And Biochemistry, 2002, vol. 40, pp. 501-507.

International Search Report for PCT International Application No. PCT/IB2019/055896, mailed on Nov. 29, 2019, 4 pages.

* cited by examiner

ASSAY

CROSS REFERENCE TO RELATED APPLICATIONS

This application is a national stage filing under 35 U.S.C. 371 of PCT/IB2019/055896, filed 10 Jul. 2019, which claims the benefit of U.S. Provisional Application No. 62/697,514, filed 13 Jul. 2018, the disclosures of which are incorporated by reference in their entireties herein.

BACKGROUND

Solution phase luminescence assays are known, for example in WO2010099486. Known assays detect the presence or amount of a substance based on specific recognition and binding together of specific binding partners. For example, in immunoassays an antibody binds to a particular binding partner. As another example, in nucleic acid binding assays a nucleic acid strand, such as an aptamer, binds to a specific binding partner. Some assays use chemiluminescence to create a signal and relate that signal to the amount of analyte.

SUMMARY

A method of assaying for an analyte in a sample can comprise forming a reaction mixture and admixing a trigger solution to the reaction mixture. The analyte to be assayed for may be present in the sample, though the assay may also reveal the analyte to be absent. The reaction mixture an aqueous solution comprising a chemiluminescent-labeled specific binding partner comprising a chemiluminescent label irreversibly bound to a first specific binding partner, the chemiluminescent-labeled specific bonding partner being capable of binding to the analyte to form an analyte-bound chemiluminescent labeled specific binding complex, an activator-labeled specific binding partner comprising an activator label irreversibly bound to a second specific binding partner, and a selective signal inhibiting agent.

The reaction mixture further comprises an unbound chemiluminescent substrate.

The trigger solution is capable of producing a background signal from the unbound chemiluminescent substrate and, in the presence of analyte, trigger solution is capable of producing a detectable analyte signal correlated to the amount of analyte in the sample.

A kit can include the components, other than the sample, necessary to conduct the aforementioned assay.

DETAILED DESCRIPTION

Throughout this disclosure, singular forms such as "a," "an," and "the" are often used for convenience; however, the singular forms are meant to include the plural unless the singular alone is explicitly specified or is clearly indicated by the context. When the singular alone is called for, the term "one and only one" is typically used.

Terms such as "common," "commonly," "typically," "usual," and "usually" are used to refer to features that are common, typical, or usual ways of making or practicing the invention(s) described herein. Those terms are not to be construed to mean that such features are present in the prior art, much less that they are common, typical, or usual, in the prior art.

Some terms in this disclosure are defined below. Other terms will be familiar to the person of skill in the art, and should be afforded the meaning that a person of ordinary skill in the art would have ascribed to them.

Analyte: a substance to be detected or quantified in an assay. One or more substances having a specific binding affinity to the analyte, and particularly one or more specific binding partners, are typically used in the assay to facilitate detection of an analyte. The analyte can be a protein, peptide, nucleotide, nucleoside, antibody, hapten, small molecule (i.e., non-polymeric molecule), or the like to which a specific binding partner can bind. Exemplary analytes include not only drugs such as steroids, hormones, proteins, glycoproteins, mucoproteins, nucleoproteins, phosphoproteins, opiods, vitamins, antibacterials, antifungals, antivirals, purines, antineoplastic agents, amphetamine, azepines, prosteglandins, as well as metabolites of drugs, but also nucleosides, organonucleosides, nucleotides, organonucleotides, ribosides, DNA, DNA segments, RNA, RNA segments, PDNA, PDNA segments, aptamers, toxins such as hemotoxins, phototoxins, neurotoxins, cyanotoxins, dinotoxins, necrotoxins, myotoxins, mycotoxins, such as T-2 mycotoxin, aflatoxins, botulism toxin, ricin, apitoxin, and other environmental toxins or biotoxins. Analytes can also be cells, viruses, bacteria, or fungi.

Activator: a compound that effects the activation of a chemiluminescent compound so that, in the presence of a trigger, the chemiluminescent compound luminesces.

Activator-labeled specific binding partner: a reactant that includes a specific binding member for an analyte and an activator directly or indirectly (e.g., through a linker) bound to the specific binding partner.

Chemiluminescent compound: a compound that undergoes a reaction causing the emission of light, for example by being converted into another compound formed in an electronically excited state or by being converted to an electronically excited state and then relaxing into a ground state. The excited state can be a single or triplet excited state. The excited state may emit light directly upon relaxation to the ground state, or may first transfer energy, such as by a Forester or Dexter mechanism, to an energy acceptor that in turn emits light.

Chemiluminescent-labeled specific binding partner: a reactant that includes a specific binding member for an analyte and a chemiluminescent compound directly or indirectly (e.g., through a linker) bound to the specific binding partner.

Analyte signal: a signal, such as a chemiluminescent output from an assay, that relates to the amount of analyte present in a sample.

Background signal: a signal, such as a chemiluminescent output, that does not relate to the amount of analyte present in a sample.

Irreversible bond: a bond associating two moieties, typically a specific binding partner and a chemiluminescent label or a specific binding partner and an activator label, that is not broken while performing the assays described herein. An irreversible bond may be broken by some other means, such as the use of chemical compounds or under physical conditions such as temperature, that it is not exposed to during the assays described herein. Typical bonds that may be irreversible bonds include covalent bonds, ionic bonds, and the like. Two moieties that are connected by an irreversible bond are said to be "irreversibly bound." An irreversible bond is distinguished from a reversible binding interaction, such as the reversible binding of specific bonding partners or of an analyte to a specific bonding partner.

Prior art chemiluminescence based-assays binding assays, such as the immunoassays described in US20100267071, as well as other assays such as those based on aptamer binding, etc., compare the chemiluminescence signal of a test sample with unknown concentration of analyte with a standard curve that is generated by using a plurality of samples with known concentration of analyte.

In a specific chemiluminescent assay, as described for example in US20100267071, a test sample containing an unknown concentration of analyte is admixed with an assay solution containing a chemiluminescent-labeled specific binding partner, an activator-labeled specific binding partner, and a selective signal inhibiting agent to form a reaction mixture. A trigger solution is then admixed with the reaction mixture. The trigger solution contains an oxidation or reducing agent, typically a peroxide, and in many cases an enhancer.

The assay proceeds in one of two formats. In a "competitive assay" format, the activator-labeled specific binding partner binds to the chemiluminescent-labeled specific binding partner in a complex that may be pre-formed or may form in situ. When analyte is present, the analyte and the chemiluminescent-labeled specific binding partner compete to bind the analyte. In the presence of a trigger solution, the chemiluminescent label on chemiluminescent-labeled specific binding partner that is bound to activator-labeled specific is in operable proximity to, and is therefore activated by, the activator-labeled specific binding partner causing luminescence. Chemiluminescent-labeled specific binding partner that is bound to analyte is not in operable proximity to the activator-labeled specific binding partner, and therefore its chemiluminescent label is not activated and it does not luminesce. In this format, the analyte signal is the luminescence intensity and it is inversely related to the analyte concentration.

An alternative is a "sandwich assay" format whereby the activator-labeled specific binding partner and the chemiluminescent-labeled specific binding partner both bind with the analyte, typically on different portions of the analyte, to bring the chemiluminescent label in operable proximity with the activator-labeled binding partner. The chemiluminescent label of the chemiluminescent-labeled specific binding partner in the resulting "sandwich" complex is in operable proximity to the activator-labeled specific binding partner and therefore luminesces. In the absence of analyte, the activator-labeled binding partner is not in operable proximity to the activator-labeled specific binding partner and therefore does not luminesce. In this format, the analyte signal is the luminescence intensity and it is directly related to the analyte concentration.

In either case, the intensity of the analyte signal in the test sample is measured in a luminometer and compared to a standard curve of luminescence intensity vs. concentration that is constructed by performing the same assay with standard samples having known concentrations of analyte. Correlating the analyte signal to the standard curve then provides a concentration of the analyte.

While this may be acceptable when the sample being analyzed contains only analyte and water, most commercial applications of chemiluminescence will also contain other substances besides the analyte. For example, when a test sample from a food substance is being assayed for the presence of a toxin, then many chemical compounds, such residual compounds from the food substance, will generally be present in addition to the toxin. These other compounds can interfere with the production of analyte signal, typically by interfering with the oxidation or reduction reactions that produces the chemiluminescent species. In this case, the correlation of the analyte signal to the standard curve will not provide an accurate concentration of the analyte in the test sample because the standard curve will be generated from solutions that do not contain these other interfering compounds. This results in a correlation error wherein the comparing the analyte signal to the standard curve does not accurately provide the concentration of the analyte in the test sample. For example, one selective signal inhibiting agent that can be used is ascorbic acid, which is also found in many food substances either naturally or as an added antioxidant. If a significant amount of ascorbic acid is present in the test sample, then it can further inhibit production of the analyte signal from the test sample and the concentration obtained by correlation of the analyte signal to the standard curve can be too low. This can be a significant problem, particularly when a harmful food contaminant is being assayed for, because the assay can incorrectly suggest that a food has safe levels of contaminant when in fact the food has unsafe levels of contaminant.

More generally, the errors in analyte concentration that can result from the interference of other compounds in the sample being assayed can be significant, in some cases as much as 40% or even greater. In the example of analyzing a food sample for toxins, some toxins are unsafe for animal consumption at levels as low as 5 ppb or even lower. Thus, these errors can mean the difference between, on the one hand, discarding a food sample that is in fact safe to consume, or on the other hand providing the false belief that a toxin is present at a safe level when in fact it is present at an unsafe level that may cause illness or death in an animal that consumes it.

Prior art solutions to this problem have not been acceptable. Removing compounds other than the analyte from the test sample to prevent interference with binding is exceptionally difficult and impractical, if not impossible, to achieve in a commercial setting, where thousands, tens of thousands, or even more different compounds of unknown identity may be present in the test sample. Another unacceptable prior art solution is to significantly dilute the test sample to the point where interference of compounds other than the analyte is negligible. This solution is unacceptable because the analyte concentration is also diluted and therefore the lowest level of detection ("LLD") and lowest level of quantification (LLQ) of the analyte is reduced. As indicated above, the concentration of many relevant analytes needs to be determined to the ppb levels, so the reductions in LLQ and LLD make a solution involving substantial dilution of the test sample unacceptable.

Not only should an acceptable solution avoid the aforementioned shortcomings, that is, it should be practical to use in a commercial setting and not require significant dilution of the test sample, but it should also be workable with a variety of binding agents, meaning that the technology should not depend on the nature of the binding partner (e.g., antibody, aptamer, etc.) such that it can be applied to a variety of different types of binding assays.

The present disclosure provides such a technical solution. Briefly, the technical solution, which is described in more detail below, involves the use of a chemiluminescent substrate as a background agent. The background agent provides a luminescent background signal in the presence of the trigger solution (by way of the same series of oxidation or reduction reactions that cause the analyte signal from the chemiluminescent label), but independently of the binding of analyte to the chemiluminescent-labeled specific binding partner. That is, the background agent need not bind to any of the binding partners in order to produce a background signal. The background agent is present, in identical known quantities, in the standards used to construct the standard curves. It is also present in the same concentration in the assay solution along with the chemiluminescent-labeled binding partner. Thus, in a situation where no compounds interfere with the oxidation or reduction reactions that the analyte signal and background signal (e.g., the analyte is the only dissolved compound in the test sample), the background signal in the test sample will be identical to the background signal in the standard sample. However, when interfering compounds are present, then the background signal from the test sample will be different from the background signal from the standard sample. The ratio of the background signal from the standard sample to the background signal from the test sample is taken to provide a scale factor. Multiplying the scale factor by the observed analyte signal provides a "corrected analyte signal," that has been corrected for the presence of interfering compounds. Correlating the corrected analyte signal, rather than the observed analyte signal, to the standard curve provides an accurate indication of the concentration of analyte in the test sample.

Specific Binding Partners

Two labeled specific binding partners are employed: one is activator-labeled and the other is chemiluminescent-labeled. Each of the specific binding partners is a molecule, usually a biological molecule, with a specific affinity for another substance. Examples include DNA, RNA, oligonucleotides, aptamers, antigens, antibodies, antibody-DNA chimeras, haptens, proteins, peptides, lectins, avidin, streptavidin, and biotin.

Each specific binding partner is generally non-identical to the other partner in that the two specific binding partners do not compete for the same or overlapping binding site on an analyte. For a typical case where the specific binding partner portion of both the activator-labeled specific binding partner and the chemiluminescent-labeled specific binding partner are antibodies, each of the antibodies has a different, non-competing epitope on the analyte.

Examples of specific binding partners that may be used in combination, that is, one can have a chemiluminescent label and the other can have an activator label, include complimentary oligonucleotides or polynucleotides, such as DNA, RNA, aptamers, and the like, avidin-biotin, streptavidin-biotin, hormone-receptor, lectin-carbohydrate, IG protein A-binding protein receptor, nucleic acid-nucleic acid binding protein, aptamer-aptamer, and nucleic acid-anti nucleic acid antibody. The specific binding partners discussed in US20100267071 are suitable.

Any of these can be adapted for a competitive assay format or a sandwich assay format. The identity of the specific binding partners determines the format of the assay, specifically, whether the assay is a sandwich assay or a competitive assay. In either case, the specific binding partner used for the chemiluminescent-labeled specific binding partner is selected to specifically bind analyte. Most commonly an antibody is used but any of the specific binding partners discussed above can also be employed. To adapt for a competitive assay format, the activator-labeled specific binding partner is designed as an activator-analyte analog conjugate. In this case, the activator is conjugated, directly or by way of a linker comprising an auxiliary substance as discussed herein, to an analog of the analyte, which may be the analyte itself or a compound with sufficient structural similarity to the analyte that it also binds to the chemiluminescent-labeled specific binding partner in essentially the same manner as the analyte.

To adapt for a sandwich assay format, both the chemiluminescent-labeled specific binding partner and the activator-labeled specific binding partner specifically bind to the analyte. In this case, the specific binding partner used for the activator-labeled specific binding partner is typically an antibody, but it may also be an aptamer or any of the specific binding partners discussed above. In this case, both the chemiluminescent-labeled specific binding partner and the activator-labeled specific binding partner bind to the analyte, typically to different binding sites on the analyte.

Both competitive and sandwich assays are known in the art, and the methods for accomplishing these adaptations are known. Examples and additional details regarding the assay formats and the specific binding partners can be found in US20100267071.

Chemiluminescent-Labeled Specific Binding Partner

The chemiluminescent-labeled specific binding partner is typically present in the reaction mixture at a concentration of less than $10^{-4}$M, particularly less than $10^{-6}$ M, and most particularly $10^{-11}$ M to $10^{-7}$M.

The chemiluminescent-labeled specific binding partner includes a specific binding partner that is labeled, usually by way of an irreversible bond, with a chemiluminescent label. Typically, each molecule of specific binding partner has at least one chemiluminescent label irreversibly bound thereto. In some cases, there may be as many as $10^2$ or even more chemiluminescent labels bound to each specific binding partner. It is not necessary that each specific binding partner molecule has the same number of chemiluminescent labels.

One or more chemiluminescent labels can be any suitable chemiluminescent moiety that can be bound, typically by way of an irreversible bond, to the specific bonding partner. The bond, typically irreversible bond, can be a direct connection or an indirect connection. In a direct connection, the one or more chemiluminescent labels are connected directly to the specific bonding partner without the use of a linker or auxiliary substance between the one or more chemiluminescent labels and the specific bonding partner. Direct connections are typically by way of an irreversible bond, such as an ionic bond, covalent bond, hydrophobic interaction, hydrogen bond, or the like, and most often a covalent bond.

When an indirect connection is employed, a linker, sometimes referred to in the art as an auxiliary substance, is used to connect the one or more chemiluminescent labels and the specific binding partner. Any suitable linker can be used; suitable linkers will not prevent the one or more chemiluminescent labels from luminescing, and typically will not make the chemiluminescent-labeled specific binding partner insoluble in aqueous media. Exemplary linkers include proteins, such as streptavidin, avidin, neutravidin, biotin, cationized BSA, fos, jun, keyhole hemocyanin, immunoglobulins (including fragments or portions thereof), liposomes, micelles, synthetic dendrimers such as AMAM, synthetic polymers such as polyacrylic acid, natural polymers such as polysaccharides, for example functionalized dextran, polynucleotides, aptamers, and oligonucleotides, and the like. Polyasaccharides, particularly amino-dextran or carboxyl-dextran, and self-assembling proteins, are most commonly employed.

The chemiluminescent label is formed by reacting a compound of the general formula CL-L-RG, wherein CL represents a chemiluminescent moiety, L represents a linker or covalent bond, and RG represents a reactive group, with a specific binding partner. Once the reaction is complete, the chemiluminescent moiety becomes a chemiluminescent label on the chemiluminescent-labeled specific binding partner. The chemiluminescent label reacts with the oxidation or reducing agent in the trigger solution or with the activator label in the activator-labeled specific binding partner to form an activated chemiluminescent compound, which is typically an excited state of the chemiluminescent label. The excited state can be either a singlet or triplet excited state. The excited state can either relax with luminescence or it can undergo energy transfer to an emissive energy acceptor which in turn luminesces. In particular embodiments, the luminescence occurs very rapidly after addition of the trigger solution, more particularly reaching peak intensity within 2 seconds of the addition of the trigger solution. However, this is not required because a slower reaction can also give accurate results so long as the analyte signal is measured over a sufficient period of time.

A wide variety of chemiluminescent compounds that are suitable for binding to a specific binding partner, such as an antibody or antibody fragment, are known in the art. Any of these can be employed in the assays described herein.

Exemplary chemiluminescent moieties and chemiluminescent labels include aromatic cyclic diacylhydrazines such as luminol, isoluminol, aminobutylethylisoluminol, aminohexylethylisoluminol, 7-dimethylaminonaphthalene-1,2-dicarboxcylic acid hydrazine, ring substituted aminophthalhydrazides, anthracene-2,3-dicarboxylic acid hydrazides, phenanthrecene-1,2-dicarboxylic acid hydrazides, pyrenedicarboxylic acid hydrazides, 5-hydroxyphthalhydrazide, 6-hydroxyphthalhydrazide, xanthene dyes such as fluorescein, eosin, rhodamine dyes, rhodol dyes, chemiluminescent aromatic amines or heterocyclic amines, MCLA, indole acetic acid, isobutyraldehyde, trihydroxyaromatic compounds such as pyrogallol, phloroglucinol, and purpurogallin, as well as the phthalazinedione compounds disclosed in U.S. Pat. Nos. 5,420,275 and 5,324,835, acridan ketenedithioacetal compounds, and combinations of the foregoing. While any of these labels may be used either with or without an emissive energy acceptor, isobutyraldehyde is most often used with an emissive energy acceptor.

Some chemiluminescent labels can be labels of the Formula I:

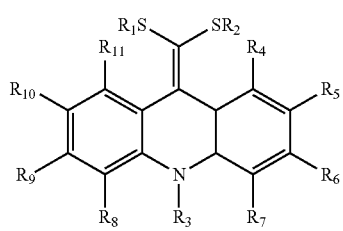

I

In labels of Formula I, each of $R_1$ and $R_2$ is independently H or an organic moiety containing from 1-50 atoms selected from C, N, O, S, P, Si, and halogen, plus sufficient hydrogen atoms to satisfy the valences of the non-hydrogen atoms. Most commonly, each of $R_1$ and $R_2$ is independently a linker to the specific binding partner, H, alkyl, substituted alkyl, alkenyl, substituted alkenyl, alkynyl, substituted alkynyl, aryl, substituted aryl, aralkyl, or substituted aralkyl. When $R_1$ and $R_2$ is substituted, it is most commonly substituted with 1-3 radicals selected from carbonyl, carboxyl, tri (alkyl) silyl, glycosyl, —$SO_3^-$, —$OSO_3^-$, —$PO_3^-$, —$OPO_3^-$, halogen, hydroxy, thiol, amino, quaternary ammonium, and quaternary phosphonium.

In labels of Formula I, $R_3$ is an H or an organic moiety containing from 1-50 atoms, most commonly from 1-20 atoms, selected from C, N, O, S, P, Si, and halogen, plus sufficient hydrogen atoms to satisfy the valences of the non-hydrogen atoms. Most commonly, $R_3$ is a linker to the specific binding partner, H, alkyl, substituted alkyl, alkenyl, substituted alkenyl, alkynyl, substituted alkynyl, aryl, substituted aryl, aralkyl, or substituted aralkyl. In such cases, $R_3$ most often has 1-20 carbon atoms. In many cases, $R_3$ is alkyl having from 1 to 4 carbon atoms, phenyl, benzyl, substituted benzyl, alkoxyalkyl, carboxyalkyl, or alkylsulfonic acid. It is possible that $R_3$, particularly when it is alkyl, substituted alkyl, alkenyl, or substituted alkenyl, but also in other cases, is covalently bound to $R_7$ or $R_8$ to form a ring, typically a five or six membered ring. When one or more of the above-mentioned moieties are substituted, it is most commonly substituted with 1-3 radicals selected from carbonyl, carboxyl, tri (alkyl) silyl, glycosyl, —$SO_3^-$, —$OSO_3^-$, —$PO_3^-$, —$OPO_3^-$, halogen, hydroxy, thiol, amino, quaternary ammonium, and quaternary phosphonium.

In labels Formula I, each of $R_4$—$R_{11}$ is independently H or an organic moiety containing from 1-50 atoms selected from C, N, O, S, P, Si, and halogen, plus sufficient hydrogen atoms to satisfy the valences of the non-hydrogen atoms. Most commonly, each of $R_1$ and $R_2$ is independently a linker to the specific binding partner, H, alkyl, substituted alkyl, alkenyl, substituted alkenyl, alkynyl, substituted alkynyl, aryl, substituted aryl, aralkyl, substituted aralkyl, alkoxy, aryloxy, halogen, amino, substituted amine, carboxyl, carboalkoxy, carboxyamide, cyano, or sulfonate. Pairs of proximal $R_4$—$R_{11}$ moieties, such as $R_4$ and $R_5$, $R_8$ and $R_9$, etc. can be covalently bound to form a ring. In this case, the ring is typically a five to seven membered ring and most typically a five or six membered ring. The ring can be carbocyclic or heterocyclic, and in the latter case can contain herteroatoms such as N, O, or S, and can be unsubstituted or substituted either on one or more carbon atoms or one or more heteroatoms. When one or more of the above-mentioned moieties are substituted, it is most commonly substituted with 1-3 radicals selected from carbonyl, carboxyl, tri (alkyl) silyl, glycosyl, —$SO_3^-$, —$OSO_3^-$, —$PO_3^-$, —$OPO_3^-$, halogen, hydroxy, thiol, amino, quaternary ammonium, and quaternary phosphonium.

Most commonly, in Formula I, each of $R_4$—$R_{11}$ H.

Most commonly, the labels of Formula I that are employed are labels of Formula II

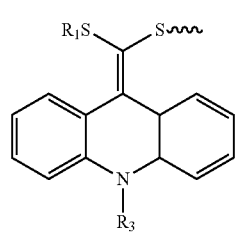

II wherein the wavy line indicates the point of attachment to the specific binding partner. In such cases, $R_3$ is typically H, alkyl, substituted alkyl, alkenyl, substituted alkenyl, alkynyl, substituted alkynyl, aryl, substituted aryl, aralkyl, or substituted aralkyl. In such cases, $R_3$ most often has 1-20 carbon atoms, particularly alkyl having from 1 to 4 carbon atoms, phenyl, benzyl, substituted benzyl, alkoxyalkyl, carboxyalkyl, or alkylsulfonic acid. When one or more of the above-mentioned moieties are substituted, it is most commonly substituted with 1-3 radicals selected from carbonyl, carboxyl, tri (alkyl) silyl, glycosyl, —$SO_3^-$, —$OSO_3^-$, —$PO_3^-$, —OPO$_3^-$, halogen, hydroxy, thiol, amino, quaternary ammonium, and quaternary phosphonium.

In particular labels of Formula II, the wavy line designates the site of attachment to the specific binding partner or to a linker connecting the compound to the specific binding partner, R$^1$, R$^2$, and R$^3$ are independently selected from substituted alkyl, unsubstituted alkyl, substituted alkyenyl, unsubstituted alkenyl, substituted alkynyl, unsubstituted alkynyl, substituted aralkyl, and unsubstituted aralkyl, wherein when R$^1$ or R$^2$ is substituted it is substituted with 1-3 substituents, each substituent independently selected from carbonyl, carboxyl, trialkylsilyl, —SO$_3$, glycosyl, —PO$_3$, halogen, hydroxyl, thiol, amino, C(O)NHNH$_2$, quaternary ammonium, and quaternary phosphonium, and R$^3$ is selected from substituted alkyl, unsubstituted alkyl, substituted alkyenyl, unsubstituted alkenyl, substituted alkynyl, unsubstituted alkynyl, substituted aralkyl, and unsubstituted aralkyl, wherein when R$^1$ or R$^2$ is substituted it is substituted with 1-3 substituents, each substituent independently selected from carbonyl, carboxyl, trialkylsilyl, —SO$_3$, glycosyl, —PO$_3$, halogen, hydroxyl, thiol, amino, C(O)NHNH$_2$, quaternary ammonium, and quaternary phosphonium.

Labels of Formula II are bound to the specific binding partner by reaction of the specific binding partner with a compound of Formula III.

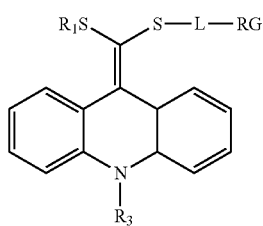

III wherein L and RG are as described above.

Examples of compounds of Formula III that can be employed are provided in Table 8 of US20100267071. Compounds of Formula I generally, and Formula III specifically, can be prepared according to methods disclosed in US20070172878. For example, a commercially available acridan or N-substituted acridan can be treated with strong base followed by carbon disulfide to form an acridan dithiocarboxylate, which is in turn esterified or partially esterified by conventional esterification methods to install substituent R$_1$. R$_2$ can be added by deprotonation of the remaining thiol with a strong base such as butyl lithium or sodium hydride and then treated with an appropriate electrophile to attach R$_2$. The substituents R$_1$ and R$_2$ may undergo further reactions to manipulate the functional groups thereon in order to achieve the desired compound of Formula III.

The chemiluminescent label can also be selected from aromatic cyclic dialhydrazides, trihydroxyaromatic compounds, acridan ketenedithioacetal compounds, acridan esters, acridan thioesters, acridan enols, and compounds having the formula

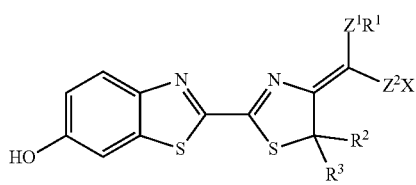

wherein
R$_1$ is selected from alyl, alkenyl, alkynyl, aryl, and aralkyl groups of 1-20-carbons or any of the foregoing substituted with 1-3 groups moieties that are independently selected from carbonyl, trialkyl silyl, SO$_3$—, —OSO$_3$, glycosyl, PO$_3$—, —OPO$_3$, halogen, hydroxyl, thiol, amino, quaternary ammonium, or quaternary phosphonium, X is selected from C1-C8 alkyl, aryl, aralkyl, alkyl or alkyl carbonyl having 1-20 carbon atoms, trialkyl silyl, SO$_3$—, glycosyl, and PO(OR')(OR") wherein R' and R" are independently selected from C1-C8 alkyl, cyanoalkyl, cyanoaryl, cyanoaralkyl, trialkylsilyl, alkali metal cation, alkaline earth cation, ammonium cation, and trianlkylphosphonium cation, Z$^1$ and Z$^2$ are independently selected from O and S atoms, and R$_2$ and R$_3$ are independently selected from H and C1-C8 alkyl.

Still further chemiluminescent labels are disclosed in U.S. Pat. No. 5,497,072, U.S. Pat. No. 523,212, U.S. Pat. Nos. 5,593,845, 5,922,588, 60,130,803, 6,696,569, 6,891,057, and US20100267071. Any of these or other chemiluminescent labels can be employed. Particularly suitable chemiluminescent labels and chemiluminescent-labeled specific binding partners include those disclosed in US20100267071.

Activator-Labeled Specific Binding Partner

The activator-labeled specific binding partner is typically present in the reaction mixture at a concentration of less than $10^{-4}$M, particularly less than $10^{-6}$ M, and most particularly $10^{-11}$ M to $10^{-7}$M.

The activator-labeled specific binding partner includes an activator label that is bound typically irreversibly bound, to a specific binding partner. Any suitable activator label can be used. A compound can be suitable to be an activator label when it meets two requirements. First, it can be able to accept or donate an electron, or in some rare cases multiple electrons, from or to the oxidation or reducing agent to form a radical, ion-radical, or, in uncommon cases, an ion. Such radical, ion-radical, or ion is sometimes referred to as an activated activator label, and the formation of an activated activator label is sometimes referred to as activating the activator label. Second, once an activated activator label is formed, it should be able to activate the chemiluminescent label on the chemiluminescent-labeled specific binding partner, and if applicable to the unbound chemiluminescent substrate, causing the chemiluminescent label, and if applicable the unbound chemiluminescent substrate, to luminesce.

Typical activator labels are peroxidases or compounds having peroxidase-like activity. Examples include lactoperoxidase, microperoxidase, myeloperoxidase, haloperoxidase, vanadium bromoperoxidase, horseradish peroxidase, fungal peroxidases, lignin peroxidase, Mn-dependent peroxidase, soybean peroxidases, and peroxidase mimetic compounds that are not enzymes but that have peroxidase-like activity such as Mn-TPPS4.

The activator-labeled specific binding partner can include conjugates or complexes of a peroxidase or compound having peroxidase-like activity with a biological molecule. In such cases, typical biological molecules that can be employed include DNA, RNA, aptamers, antibodies, antibody fragments, antibody-DNA chimeras, antigens, haptens, proteins, peptides, lechtins, avidin, streptavidin, and biotin.

One or more activator labels are bound, typically by way of an irreversible bond, to the specific bonding partner. The bond, typically irreversible bond, can be a direct connection or an indirect connection. In a direct connection, the one or more chemiluminescent labels are connected directly to the specific bonding partner without the use of a linker or auxiliary substance between the one or more chemiluminescent labels and the specific bonding partner. Direct connections are typically by way of an irreversible bond, such as an ionic bond, covalent bond, hydrophobic interaction, hydrogen bond, or the like, and most often a covalent bond.

When an indirect connection is employed, a linker, sometimes referred to in the art as an auxiliary substance, is used to connect the one or more chemiluminescent labels and the specific bonding partner. Any suitable linker can be used; suitable linkers will not prevent the one or more chemiluminescent labels from luminescing, and typically will not make the chemiluminescent-labeled specific binding partner insoluble in aqueous media. Exemplary linkers include proteins, such as streptavidin, avidin, neutravidin, biotin, cationized BSA, fos, jun, keyhole hemocyanin, immunoglobulins (including fragments or portions thereof), liposomes, micelles, synthetic dendrimers such as AMAM, synthetic polymers such as polyacrylic acid, natural polymers such as polysaccharides, for example functionalized dextran, polynucleotides, aptamers, and oligonucleotides, and the like. Polyasaccharides, particularly amino-dextran or carboxyl-dextran, and self-assembling proteins, are most commonly employed.

Suitable activator-labeled specific binding partners include those disclosed in US20100267071.

Selective Signal Inhibiting Agents

Selective signal inhibiting agents reduce the noise signal caused by excess chemiluminescent-labeled specific binding partner that is present in the reaction mixture but does not participate in the assay described herein. Their function is described in more detail in US20100267071.

Typically, one or more selective signal inhibiting agents are present in the reaction mixture at a concentration of $10^{-6}$ M to $10^{-1}$ M, most often $10^{-5}$ M to $10^{-4}$ M. Particular concentrations include $5 \times 10^{-6}$ M to $5 \times 10^{-4}$ M, and more particularly $5 \times 10^{-5}$ M to $5 \times 10^{-4}$ M.

Compounds that are suitable for use as selective signal inhibiting agents include anti-oxidants, particularly sacrificial anti-oxidants, as well as other molecules that can react with the radical, ion-radical, or in some cases ion, formed by the oxidation or reducing agent interacting with the activator label on the activator-labeled selective binding partner or, in some cases, the oxidation or reducing agent. Any anti-oxidant can be employed, because for the purposes of this disclosure the various options for selective signal inhibiting agents function in the same way. Specifically, the react with the oxidation or reducing agent, which is usually a peroxide, or with the activated activator label on the activator-labeled specific binding partner, to quench the peroxide radical or the activated activator label.

Some specific anti-oxidants that can be employed as selective signal inhibiting agents are described in US20100267071. Examples include glutathione, ascorbic acid, particularly L-ascorbic acid, salts of ascorbic acid, particularly salts of L-ascorbic acid, uric acid, L-ascorbic acid-6-palmitate, tocopherol, 5,6-isopropylidene-L-acobic acid, isoascorbic acid, including D-isoascorbic acid, L-isoasocrbic acid, or both, sodium sulfite, diethylhydroxylamine, BHT,

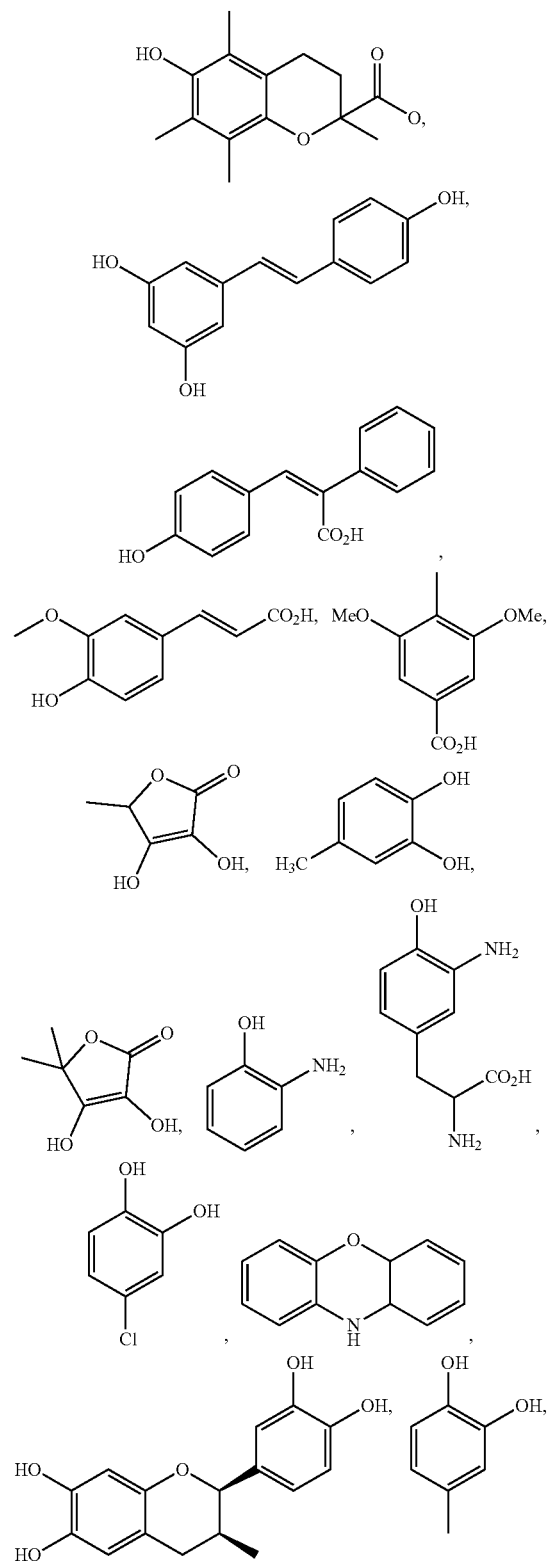

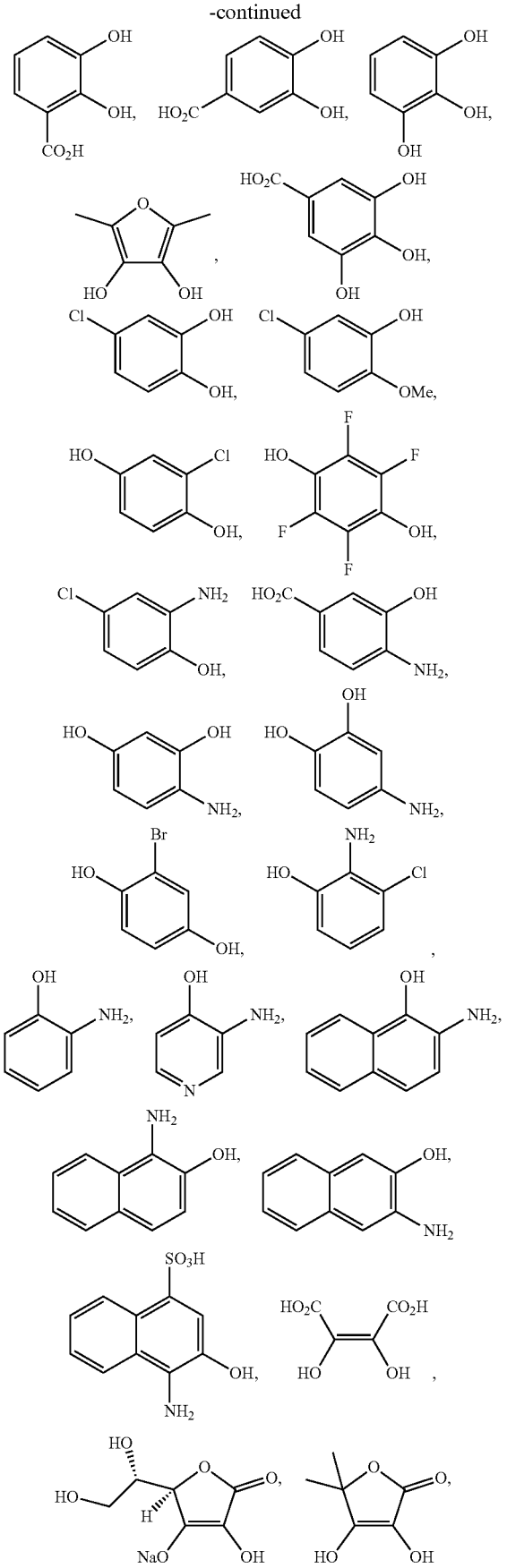
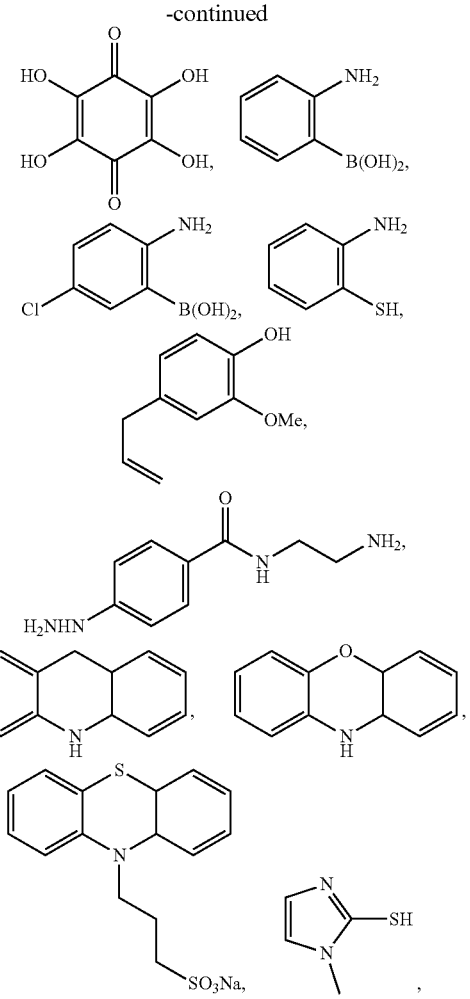

and combinations of the foregoing. Most commonly, tocopherol or ascorbic acid, and particularly ascorbic acid, is used.

In use, the one or more selective signal inhibiting agents can be provided in any suitable way. For example, they can be provided as a component of the trigger solution, in which case the reaction mixture is formed when the trigger solution is added. They can also be provided with one or both of the chemiluminescent-labeled specific binding partner or activator-labeled specific binding partner, or they can be added alone as a solid or as a solution of appropriate concentration. Most commonly, the one or more selective signal inhibiting agents are provided in a working solution at a concentration that is ten-fold higher, or in some cases even greater than ten-fold higher, than the concentration to be provided in the reaction mixture, particularly after addition of the trigger solution. The working solution is typically aqueous, and in many cases can be water, such as buffered water, but in some cases it can also contain surfactants, ethanol, glycols, and or the like in order to provide a sufficiently high concentration of the one or more selective signal inhibiting agents. In any event, they are added in an appropriate amount to achieve a suitable concentration in the reaction mixture.

Trigger Solution

The trigger solution provides one or more oxidation or reducing agents that are needed to cause luminescence from the chemiluminescent-labeled specific binding partner and, in some cases, from the background agent. The one or more oxidation or reducing agents may perform this function by reacting directly with the chemiluminescent label and, where applicable, the background agent, but more commonly the one or more oxidation or reducing agents react with the activator label on the activator-labeled specific binding partner to facilitate the action of the activator label with the chemiluminescent label.

The one or more oxidation or reducing agents can be any compounds that activate the activator label on the activator-labeled specific binding partner. Most commonly, the one or more oxidation or reducing agents are one or more peroxides that interact with the activator label, which typically is a peroxidase or a compound having peroxidase-like activity, to activate the activator label. While any peroxide that reacts with the peroxidase or a compound having peroxidase-like activity can be used, commonly used peroxides include alkyl peroxides, particularly wherein the alkyl is ethyl or methyl, alkyl hydroperoxides, particularly where the alkyl is ethyl or methyl, aromatic peroxides, particularly benzyl peroxide, lipid hydroperoxides, particularly the hydroperoxides of eicosapentaeonic acid, docosahexanoic acid, or linoleic acid, peroxy acids such as meta-chloroperoxybenzoic acid, hydrogen peroxide, urea peroxide, carbamate peroxide, and perborates. The concentration of the peroxide can vary, but is typically from $10^{-8}$ M to 3M, and most commonly $10^{-3}$ M to $10^{-1}$ M.

While not required, an enhancer is typically used as a component of the trigger solution. The enhancer can be any compound that promotes the reactivity of the activator label, typically a peroxidase enzyme, reduces noise signal in the assay, or both. Typical enhancers include phenolic compounds, aromatic amines, mixtures of phenoxazine or phenothizine with an indophenol or indoaniline, substituted hydroxybenzoxazoles, substituted or unsubstituted arylboronic acids as well as their esters and anhydrides, and the like. Some suitable enhancers are disclosed in US20100267071, U.S. Pat. Nos. 5,171,668, 5,206,149, and 5,512,451. When employed, an enhancer is typically present at a concentration of $10^{-5}$ M to $10^{-1}$ M As discussed above, the one or more selective signal inhibiting agents can be present in the trigger solution in addition to the oxidation or reducing agent and, when employed, the enhancer.

The trigger solution typically contains the various solutes described in an aqueous solvent. The aqueous solvent is typically buffered water. Any buffer useful with biological systems can be employed so long as it does not interfere with the luminescence of the chemiluminescent label or the assay to the point where a sufficient analyte signal cannot be produced. Most useful buffers will maintain a pH of 5 to 10.5. Particularly useful buffers maintain a pH of 6.0-9.0, such as 65.-8.5, and most particularly 7.0-8.0

Exemplary buffers that can be used are disclosed in US20100267071. Most commonly, the buffer is selected from phosphate, borate, acetate, tris(hydroxy-methylamine) methane, glycine, tricine, 2-amino-2-methyl-1-propanol, diethanolamine, MOPS, HEPES, MES, and the like.

One or more detergents or polymeric surfactants can be used to enhance luminescence or decrease the noise signal. Examples include polyoxyethylenated alkyl phenols, polyoxyethhylenated alcohols, polyoxyethylenated ethers, polyoxyethylenated sorbitol esters, quaternary ammonium salts such as CTAB, and quaternary phosphonium salts. Particularly useful examples are polymeric cationic surfactants, most particularly quaternary ammonium salts and quaternary phosphonium salts.

As discussed above, the one or more selective signal inhibiting agents can optionally be present in the trigger solution.

As an example, a trigger solution can contain an aqueous buffer, a peroxide at a concentration of $10^{-5}$ M to 1 M, and an enhancer at a concentration of $10^{-5}$ M to $10^{-1}$ M. As another example, a trigger solution can contain an aqueous buffer, a peroxide at a concentration of $10^{-5}$ M to 1 M, an enhancer at a concentration of $10^{-5}$ M to $10^{-1}$ M, and one or more selective signal inhibiting agents at a concentration such that the one or more selective signal inhibiting agents has a concentration of $10^{-6}$ M to $10^{-1}$ M in the reaction mixture.

Unbound Chemiluminescent Substrate

The unbound chemiluminescent substrate can be any chemiluminescent molecule that is not conjugated or otherwise irreversibly bond to the analyte-labeled selective binding partner or the chemiluminescent-labeled specific binding partner. In most cases, the unbound chemiluminescent substrate is soluble in the reaction mixture. To separately measure the luminescence intensity of the chemiluminescent-labeled specific binding partner and the unbound chemiluminescent substrate, it can be convenient to select an unbound chemiluminescent substrate that has a wavelength of maximum luminesce that is different from the wavelength of maximum luminescence of the chemiluminescent label, but this is not required.

During the assay, the unbound chemiluminescent substrate can react with the oxidation or reducing agent, most often indirectly by way of the activator label on the activator-labeled specific binding partner. This reaction brings the chemiluminescent substrate into an electronically excited state from which it can luminesce to produce a background signal. Alternatively, but less typically, the excited state of the unbound chemiluminescent substrate can undergo further reaction with an emissive energy acceptor, which in turn can luminesce to produce a background signal.

Suitable unbound chemiluminescent substrates include cyclic hydrazides such as luminol and isoluminol, imidazole compounds such as lophine, acridinium esters such as lucigenin and acridan, phthalhydrazides such as 2,3-dihydro-1, 4-phthalazinedione, luciferin, and 1,2 dioxyetane containing compounds such as dione, 3-(2'-spiroadamantane)-4-methoxy-4-(3"-phosphoryloxy)phenyl-1,2-dioxetane (AMPPD), and, 3-(2'-spiroadamantane)-4-methoxy-4-(3"-beta-D'-galactopyrano-yloxy)phenyl-1,2-dioxetane (AMPGD), disodium 3-(4-methoxyspiro {1,2-dioxetane-3, 2'-(5'-chloro)tricyclo [3.3.1.13,7]decan}-4-yl)phenyl phosphate, and 1,2-dioxetanedione, adamantylidene-adamantyl-1,2-dioxetane. Most common are luminol and isoluinol, and particularly luinol.

In the assay, the unbound chemiluminescent substrate is converted to an excited state that produces a detectable background signal, typically in the form of luminescence, by the same photochemical mechanism as the chemiluminescent label, namely by reaction with the oxidation or reducing agent, typically by way of the activator label. The detectable background signal is not correlated to the concentration of the analyte. Thus, non-analyte components of the sample that might interfere with the production of analyte signal will similarly interfere with the production of background signal.

It is possible to take advantage of this to obtain a correction factor that corrects for interference of non-analyte compounds with the assay. To do so, a set of standard samples are prepared, each containing a different known amount analyte, along with the other components of the reaction mixture (i.e., the chemiluminescent-labeled specific binding partner, the activator-labeled specific binding partner, and the unbound chemiluminescent substrate) are exposed to a trigger. Each of the reaction mixtures used with the standard samples has the same amount of the chemiluminescent-labeled specific binding partner, the activator-labeled specific binding partner, and the unbound chemiluminescent substrate. A trigger solution is added, and the standard samples are measured for both the analyte signal at different concentrations of analyte and for the background signal, which will normally be the same for all of the standard samples because the concentration of unbound chemiluminescent substrate is identical in all of the standard samples. If the background signal is not the same for all of the test samples, this indicates either an error on the part of the assayer, or that the analyte interacts with the unbound chemiluminescent substrate. In the latter case a different unbound chemiluminescent substrate can be employed.

The analyte signal at different concentrations of analyte can be used to make a correlation curve of analyte signal vs. analyte concentration.

The background signal from the test samples can be used to make a scale factor, as follows. A test sample is assayed and both the analyte signal and background signal are determined. A scale factor is calculated as the ratio of the background signal produced by the standard sample to the background signal produced by the test sample. This scale factor takes into account the effects of non-analyte compounds in the test sample, and is 1 if there are no non-analyte compounds in the test sample that interfere with the assay.

To determine the analyte concentration in the test sample, the analyte signal of the test sample is multiplied by the scale factor to give a corrected analyte signal. The corrected analyte signal is compared to the correlation curve of analyte signal vs. analyte concentration that was determined from the standard samples to provide the analyte concentration.

Detection

The various signals, such as background signal and analyte signal, can be detected by any art-known devices. The type of device can depend on the type of signal. When the signal is a luminescence signal, a luminometer or CCD camera is typically used. Other useful detectors include photographic film, x-ray film, scintillation counters, actinometers, transmittance detectors such as UV/Vis and IR detectors, and the like. Most commonly, detection is performed in a test tube or in multi-well plates in a luminometer or in front of a CCD camera. The use of multi-well plates and a CCD camera can be convenient because in that case it can be possible to perform assays and detection of a plurality of test samples and standard samples at the same time, each in different wells of the multi-well plate. Detection can be performed with any of the numerous commercially available or art-known luminometers, CCD cameras, etc.

Uses

The assay as described herein can find use in a variety of systems. ELISA systems are one use, but also assays involving aptamer binding and other, non-immunogen specific binding partners can be employed following the guidance herein and the knowledge of the artisan. Examples include solution hybridization assays, DNA detection in Southern blotting, RNA detection in Northern blotting, DNA or RNA sequencing, DNA or RND fingerprinting, colony hybridization, and plaque assays, all of which are known in the art. Any analyte for which at least one specific binding partner can be made can be analyzed. Examples include antigens, toxins, venoms, nucleic acids, nucleotides, polynucleotides, drugs, steroids, haptens, antibodies, peptides, peptide fragments, hormones, receptors, primers, small molecules, and the like.

List of Illustrative Embodiments

This list of embodiments is meant to aid in understanding particular aspects of the invention. It is not intended to be limiting.

1. A method of assaying for an analyte in a sample, the method comprising
    forming a reaction mixture, and admixing a trigger solution to the reaction mixture; wherein
    the analyte to be assayed for may be present in the sample,
    the reaction mixture an aqueous solution comprising
        a chemiluminescent-labeled specific binding partner comprising a chemiluminescent label irreversibly bound to a first specific binding partner, the chemiluminescent-labeled specific bonding partner being capable of binding to the analyte to form an analyte-bound chemiluminescent labeled specific binding complex,
        an activator-labeled specific binding partner comprising an activator label irreversibly bound to a second specific binding partner, and
        a selective signal inhibiting agent; and wherein
    the reaction mixture further comprises an unbound chemiluminescent substrate, and
    the trigger solution is capable of producing a background signal from the unbound chemiluminescent substrate and,
    in the presence of analyte, trigger solution is capable of producing a detectable analyte signal that is related to the amount of analyte in the sample.

2. The method of embodiment 1, wherein the reaction mixture further comprises an enhancer.

3. The method of embodiment 1, wherein the trigger solution further comprises an enhancer.

4. The method of any of the preceding embodiments, wherein the selective signal inhibiting agent causes the ratio of signal produced by reaction between the chemiluminescent-labeled specific binding partner and the activator labeled specific binding partner in a complex with the analyte to exceed the signal from reaction between the chemiluminescent-labeled specific binding partner and activator labeled specific binding partner when no complex with the analyte is present.

5. The method of any of the preceding embodiments, wherein the selective signal inhibiting agent is selected from the group consisting of aromatic compounds having at least two hydroxyl groups in an ortho or para orientation, aromatic compounds having at least one hydroxyl group and an amino group that is ortho or para to one or more of the at least one hydroxyl groups, compounds having at least two hydroxyl groups substituted on an ethyleneically unsaturated group, and nitrogen heterocyclic groups.

6. The method of any of the preceding embodiments, wherein the selective signal inhibiting agent is selected from the group consisting of ascorbic acid, isoascorbic acid, 6-hydroxy-2,5,7,8-tetramethylchroman-2-carboxylic acid, ascorbic acid 6-palmitate, 5,6-isopropylidiene-ascorbic acid, butylated hydroxy toluene, glutathione, uric acid, one or more tocopherols, and catechin.

7. The method of any of the preceding embodiments, wherein the selective signal inhibiting agent is ascorbic acid.

8. The method of any of the preceding embodiments, wherein the chemilumiescent-labeled specific binding partner comprises a chemiluminescent label connected directly or indirectly to a specific binding pair member, wherein the chemiluminescent label is selected from aromatic cyclic dialhydrazides, trihydroxyaromatic compounds, acridan ketenedithioacetal compounds, acridan esters, acridan thioesters, acridan enols, and compounds having the formula

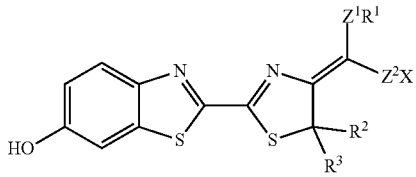

wherein $R^1$ is selected from alyl, alkenyl, alkynyl, aryl, and aralkyl groups of 1-20-carbons or any of the foregoing substituted with 1-3 groups moieties that are independently selected from carbonyl, trialkyl silyl, $SO_3$—, —$OSO_3$, glycosyl, $PO_3$—, —$OPO_3$, halogen, hydroxyl, thiol, amino, quaternary ammonium, or quaternary phosphonium;

X is selected from C1-C8 alkyl, aryl, aralkyl, alkyl or alkyl carbonyl having 1-20 carbon atoms, trialkyl silyl, $SO_3$—, glycosyl, and PO(OR')(OR") wherein R' and R" are independently selected from C1-C8 alkyl, cyanoalkyl, cyanoaryl, cyanoaralkyl, trialkylsilyl, alkali metal cation, alkaline earth cation, ammonium cation, and trianlkylphosphonium cation;

$Z^1$ and $Z^2$ are independently selected from O and S atoms; and $R^2$ and $R^3$ are independently selected from H and C1-C8 alkyl.

9. The method of any of embodiments 1-7 wherein the chemiluminescent-labeled specific binding partner comprises a chemiluminescent label connected directly or indirectly to a specific binding partner, wherein the chemiluminescent label has formula

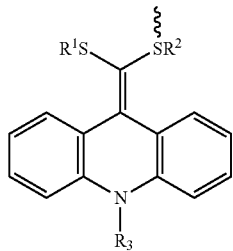

wherein the wavy line designates the site of attachment to the specific binding partner or to a linker connecting the compound to the specific binding partner;

$R^1$, $R^2$, and $R^3$ are independently selected from substituted alkyl, unsubstituted alkyl, substituted alkyenyl, unsubstituted alkenyl, substituted alkynyl, unsubstituted alkynyl, substituted aralkyl, and unsubstituted aralky groups of 1-20 carbon atoms, wherein when $R^1$ or $R^2$ is substituted it is substituted with 1-3 substituents, each substituent independently selected from carbonyl, carboxyl, tri (C1-C8)alkylsilyl, —$SO_3^-$, —$OSO_3^{2-}$-glycosyl, —$PO_3^-$, —$OPO_3^{2-}$, halogen, hydroxyl, thiol, amino, C(O)NHNH$_2$, quaternary ammonium, and quaternary phosphonium.

10. The method of any of the preceding embodiments, wherein the activator-labeled specific binding partner comprises an activator label compound connected directly or indirectly to a specific binding pair member, wherein the activator label is selected from transition metal salts, transition metal complexes, and enzymes, and wherein the activator label has peroxidase activity.

11. The method of any of the preceding embodiments, wherein the activator label is a peroxidase enzyme.

12. The method of embodiment 11 wherein the activator label is horseradish peroxidase.

13. The method of any of the preceding embodiments, wherein at least one of the chemiluminescent-labeled specific binding partner and activator-labeled specific binding partner comprises an auxiliary substance selected from soluble proteins, streptavidin, avidin, neutravidin, biotin, cationized BSA, fos, jun, soluble synthetic dendrimer, soluble synthetic polymer, polysaccharide, dextran, organonuceotide, nucleotide, nucleoside, aptamer, liposome, and micelle.

14. The method of any of embodiments 2-12, wherein the enhancer is one or more compounds that promote the catalytic turnover of an activator having peroxidase activity.

15. The method of embodiment 13, wherein the enhancer is selected from phenol compounds, aromatic amines, benzoxazoles, hydroxybenzothiazoles, aryl boronic acids, and mixtures of any of the foregoing.

16. The method of any of the preceding embodiments, wherein the trigger solution comprises an oxidation or reducing agent.

17. The method of any of the preceding embodiments, wherein the trigger solution comprises a peroxide.

18. The method of embodiment 17, wherein the peroxide is selected from the group consisting alkyl peroxides, particularly wherein the alkyl is ethyl or methyl, alkyl hydroperoxides, particularly where the alkyl is ethyl or methyl, aromatic peroxides, particularly benzyl peroxide, lipid hydroperoxides, particularly the hydroperoxides of eicosapentaeonic acid, docosahexanoic acid, or linoleic acid, peroxy acids such as meta-chloroperoxybenzoic acid, hydrogen peroxide, urea peroxide, carbamate peroxide, and perborates.

19. The method of embodiment 18, wherein the peroxide is hydrogen peroxide

20. The method of any of the preceding embodiments, wherein the trigger solution comprises an enhancer selected from phenol compounds, aromatic amines, benzoxazoles, hydroxybenzothiazoles, aryl boronic acids, and mixtures of any of the foregoing.

21. The method of any of the preceding embodiments wherein all of the components of the trigger solution and the reaction mixture as well as the analyte are water soluble.

22. The method of any of the preceding embodiments wherein none of the trigger solution, the assay solution, or the reaction mixture contain a material that is conjugated directly or indirectly to a solid phase substance.

23. The method of any of the preceding embodiments, wherein the selective signal agent comprises a compound selected from the group consisting of aromatic compounds having at least two hydroxy moieties in an ortho or para orientation, aromatic compounds having a hydroxyl moiety and an amino moiety in an ortho or para orientation, compounds having at least two vinyl hydroxyl groups, and nitrogen heterocycles.

24. The method of any of the preceding embodiments, wherein the selective signal inhibiting agent comprises ascorbic acid, and wherein the ascorbic acid is particularly L-ascorbic acid.

25. The method of any of the preceding embodiments, wherein the selective signal inhibiting agent comprises 6-hydroxy-2,5,7,8-tetramehtylchroman-2-carboxylic acid.

26. The method of any of the preceding embodiments, wherein the selective signal inhibiting agent comprises 2-amineophenol.

27. The method of any of the preceding embodiments, wherein the selective signal inhibiting agent comprises 3-amino-tyrosine, particularly 3-amino-L-tyrosine.

28. The method of any of the preceding embodiments, wherein the selective signal inhibiting agent comprises 4-chlorocatechol.

29. The method of any of the preceding embodiments, wherein the selective signal inhibiting agent comprises phenoxazine.

30. The method of any of the preceding embodiments, wherein the selective signal inhibiting agent comprises 2-bromobenzne-1,4-diol.

31. The method of any of the preceding embodiments, wherein the selective signal inhibiting agent comprises 5,6-isopropylidine ascorbic acid.

32. The method of any of the preceding embodiments, wherein the selective signal inhibiting agent comprises 6-palmitate.

33. The method of any of the preceding embodiments, wherein the chemiluminescent-labeled specific binding partner and the activator-labeled specific binding partner each bind to the analyte in the sample.

34. The method of any of the preceding embodiments, wherein the chemiluminescent-labeled specific binding partner comprises a chemiluminescent labeled compound connected to an analog of the analyte and further wherein the analyte and the chemiluminescent-labeled specific binding partner compete to bind with the activator-labeled specific binding partner.

35. The method of any of the preceding embodiments, wherein the unbound chemiluminescent substrate is selected from the group consisting of cyclic hydrazides such as luminol and isoluminol, imidazole compounds such as lophine, acridinium esters such as lucigenin and acridan, phthalhydrazides such as 2,3-dihydro-1,4-phthalazinedione, luciferin, and 1,2 dioxyetane containing compounds such as dione, 3-(2'-spiroadamantane)-4-methoxy-4-(3''-phosphoryloxy)phenyl-1,2-dioxetane (AMPPD), and, 3-(2'-spiroadamantane)-4-methoxy-4-(3''-beta-D'-galactopyrano-yloxy) phenyl-1,2-dioxetane (AMPGD), disodium 3-(4-methoxyspiro {1,2-dioxetane-3,2'-(5'-chloro)tricyclo [3.3.1.13,7]decan}-4-yl)phenyl phosphate, and 1,2-dioxetanedione, adamantylidene-adamantyl-1,2-dioxetane, particularly luminol or isoluminol, and more particularly luminol.

36. The method of any of the preceding embodiments, wherein the unbound chemiluminescent substrate comprises luminol.

37. The method of any of the preceding embodiments, wherein the wavelength of maximum luminescence intensity of the unbound chemiluminescent substrate is different from the wavelength of maximum luminescence intensity of the chemiluminescent label.

38. The method of any of the preceding embodiments, wherein the method further comprises detecting an analyte signal and a background signal.

39. The method of embodiment 38, wherein detecting an analyte signal comprises detecting at least one standard analyte signal from at least one sample that is a standard sample having a known concentration of analyte and further comprises detecting a test analyte signal from at least one test sample having an unknown concentration of analyte.

40. The method of embodiment 38 or 39, wherein detecting a background signal comprises detecting at least one standard background signal from at least one sample that is a standard sample having a known concentration of analyte and further comprises detecting a test background signal from at least one test sample having an unknown concentration of analyte.

41. A kit for assaying for an analyte, the kit comprising
a chemiluminescent-labeled specific binding partner comprising a chemiluminescent label irreversibly bound to a first specific binding partner, the chemiluminescent-labeled specific bonding partner being capable of binding to the analyte to form an analyte-bound chemiluminescent labeled specific binding complex,
an activator-labeled specific binding partner comprising an activator label irreversibly bound to a second specific binding partner, and
a selective signal inhibiting agent; and wherein
a trigger solution is capable of producing a background signal from the unbound chemiluminescent substrate, and further comprising an unbound chemiluminescent substrate; wherein
in the presence of analyte, the trigger solution is capable of producing a detectable analyte signal that is related to the amount of analyte in the sample.

42. The kit of any of embodiment 41, wherein the trigger solution further comprises an enhancer.

43. The kit of any of embodiment 41 or 42, wherein the selective signal inhibiting agent causes the ratio of signal produced by reaction between the chemiluminescent-labeled specific binding partner and the activator labeled specific binding partner in a complex with the analyte to exceed the signal from reaction between the chemiluminescent-labeled specific binding partner and activator labeled specific binding partner when no complex with the analyte is present.

44. The kit of any of embodiments 41-43, wherein the selective signal inhibiting agent is selected from the group consisting of aromatic compounds having at least two hydroxyl groups in an ortho or para orientation, aromatic compounds having at least one hydroxyl group and an amino group that is ortho or para to one or more of the at least one hydroxyl groups, compounds having at least two hydroxyl groups substituted on an ethyleneically unsaturated group, and nitrogen heterocyclic groups.

45. The kit of any of embodiments 41-44, wherein the selective signal inhibiting agent is selected from the group consisting of ascorbic acid, isoascorbic acid, 6-hydroxy-2, 5,7,8-tetramethylchroman-2-carboxylic acid, ascorbic acid 6-palmitate, 5,6-isopropylidiene-ascorbic acid, butylated hydroxy toluene, glutathione, uric acid, one or more tocopherols, and catechin.

46. The kit of any of embodiments 41-45, wherein the selective signal inhibiting agent is ascorbic acid.

47. The kit of any of embodiments 41-46, wherein the chemlumiescent-labeled specific binding partner comprises a chemiluminescent label connected directly or indirectly to a specific binding pair member, wherein the chemiluminescent label is selected from aromatic cyclic dialhydrazides, trihydroxyaromatic compounds, acridan ketenedithioacetal compounds, acridan esters, acridan thioesters, acridan enols, and compounds having the formula

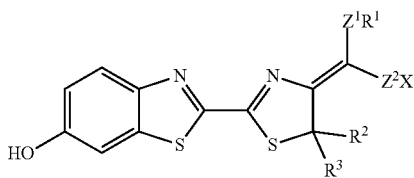

wherein
R[1] is selected from alyl, alkenyl, alkynyl, aryl, and aralkyl groups of 1-20-carbons or any of the foregoing substituted with 1-3 groups moieties that are independently selected from carbonyl, trialkyl silyl, $SO_3$—, —$OSO_3$, glycosyl, $PO_3$—, —$OPO_3$, halogen, hydroxyl, thiol, amino, quaternary ammonium, or quaternary phosphonium;

X is selected from C1-C8 alkyl, aryl, aralkyl, alkyl or alkyl carbonyl having 1-20 carbon atoms, trialkyl silyl, $SO_{3-}$, glycosyl, and PO(OR')(OR") wherein R' and R" are independently selected from C1-C8 alkyl, cyanoalkyl, cyanoaryl, cyanoaralkyl, trialkylsilyl, alkali metal cation, alkaline earth cation, ammonium cation, and trianlkylphosphonium cation;

$Z^1$ and $Z^2$ are independently selected from O and S atoms; and $R^2$ and $R^3$ are independently selected from H and C1-C8 alkyl.

48. The kit of any of embodiments 41-46 wherein the chemiluminescent-labeled specific binding partner comprises a chemiluminescent label connected directly or indirectly to a specific binding partner, wherein the chemiluminescent label has formula

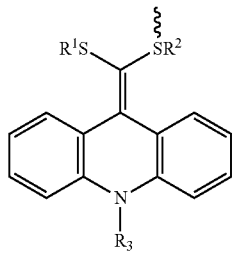

wherein
the wavy line designates the site of attachment to the specific binding partner or to a linker connecting the compound to the specific binding partner;
$R^1$ and $R^2$ are independently selected from substituted alkyl, unsubstituted alkyl, substituted alkyenyl, unsubstituted alkenyl, substituted alkynyl, unsubstituted alkynyl, substituted aralkyl, and unsubstituted aralkyl, wherein when $R^1$ or $R^2$ is substituted it is substituted with 1-3 substituents, each substituent independently selected from carbonyl, carboxyl, trialkylsilyl, —$SO_3$, glycosyl, —$PO_3$, halogen, hydroxyl, thiol, amino, C(O)NHNH$_2$, quaternary ammonium, and quaternary phosphonium;
$R^3$ is selected from substituted alkyl, unsubstituted alkyl, substituted alkyenyl, unsubstituted alkenyl, substituted alkynyl, unsubstituted alkynyl, substituted aralkyl, and unsubstituted aralkyl, wherein when $R^1$ or $R^2$ is substituted it is substituted with 1-3 substituents, each substituent independently selected from carbonyl, carboxyl, trialkylsilyl, —$SO_3$, glycosyl, —$PO_3$, halogen, hydroxyl, thiol, amino, C(O)NHNH$_2$, quaternary ammonium, and quaternary phosphonium.

49. The kit of any of embodiments 41-48, wherein the activator-labeled specific binding partner comprises an activator label compound connected directly or indirectly to a specific binding pair member, wherein the activator label is selected from transition metal salts, transition metal complexes, and enzymes, and wherein the activator label has peroxidase activity.

50. The kit of any of embodiments 41-49, wherein the activator label is a peroxidase enzyme.

51. The kit of any of embodiments 50, wherein the activator label is horseradish peroxidase.

52. The kit of any of embodiments 41-50, wherein at least one of the chemiluminescent-labeled specific binding partner and activator-labeled specific binding partner comprises an auxiliary substance selected from soluble proteins, streptavidin, avidin, neutravidin, biotin, cationized BSA, fos, jun, soluble synthetic dendrimer, soluble synthetic polymer, polysaccharide, dextran, organonuceotide, nucleotide, nucleoside, aptamer, liposome, and micelle.

53. The kit of any of embodiments 42-52, wherein the enhancer is one or more compounds that promote the catalytic turnover of an activator having peroxidase activity.

54. The kit of any of embodiment 53, wherein the enhancer is selected from phenol compounds, aromatic amines, benzoxazoles, hydroxybenzothiazoles, aryl boronic acids, and mixtures of any of the foregoing.

55. The kit of any of embodiments 41-54, wherein the trigger solution comprises an oxidation or reducing agent.

56. The kit of any of embodiments 41-55, wherein the trigger solution comprises a peroxide.

57. The kit of any of embodiment 56, wherein the peroxide compound is selected from the group consisting alkyl peroxides, particularly wherein the alkyl is ethyl or methyl, alkyl hydroperoxides, particularly where the alkyl is ethyl or methyl, aromatic peroxides, particularly benzyl peroxide, lipid hydroperoxides, particularly the hydroperoxides of eicosapentaeonic acid, docosahexanoic acid, or linoleic acid, peroxy acids such as meta-chloroperoxybenzoic acid, hydrogen peroxide, urea peroxide, carbamate peroxide, and perborates.

58. The kit of any of embodiment 57, wherein the peroxide is hydrogen peroxide.

59. The kit of any of embodiments 41-58, wherein the trigger solution comprises an enhancer selected from phenol compounds, aromatic amines, benzoxazoles, hydroxybenzothiazoles, aryl boronic acids, and mixtures of any of the foregoing.

60. The kit of any of embodiments 41-59 wherein all of the components of the trigger solution and the reaction mixture as well as the analyte are water soluble.

61. The kit of any of embodiments 41-60, wherein none of the trigger solution, the assay solution, or the reaction mixture contain a material that is conjugated directly or indirectly to a solid phase substance.

62. The kit of any of embodiments 41-61, wherein the selective signal agent comprises a compound selected from the group consisting of aromatic compounds having at least two hydroxy moieties in an ortho or para orientation, aromatic compounds having a hydroxyl moiety and an amino moiety in an ortho or para orientation, compounds having at least two vinyl hydroxyl groups, and nitrogen heterocycles.

63. The kit of any of embodiments 41-62, wherein the selective signal inhibiting agent comprises ascorbic acid, and wherein the ascorbic acid is particularly L-ascorbic acid.

64. The kit of any of embodiments 41-63, wherein the selective signal inhibiting agent comprises 6-hydroxy-2,5, 7,8-tetramehtylchroman-2-carboxylic acid.

65. The kit of any of embodiments 41-64, wherein the selective signal inhibiting agent comprises 2-amineophenol.

66. The kit of any of embodiments 41-65, wherein the selective signal inhibiting agent comprises 3-amino-tyrosine, particularly 3-amino-L-tyrosine.

67. The kit of any of embodiments 41-66, wherein the selective signal inhibiting agent comprises 4-chlorocatechol.

68. The kit of any of embodiments 41-67, wherein the selective signal inhibiting agent comprises phenoxazine.

69. The kit of any of embodiments 41-68, wherein the selective signal inhibiting agent comprises 2-bromobenzne-1,4-diol.

70. The kit of any of embodiments 41-69, wherein the selective signal inhibiting agent comprises 5,6-isopropylidine ascorbic acid.

71. The kit of any of embodiments 41-70, wherein the selective signal inhibiting agent comprises 6-palmitate.

72. The kit of any of embodiments 41-71, wherein the chemiluminescent-labeled specific binding partner and the activator-labeled specific binding partner are each adapted to bind to the analyte in the sample.

73. The kit of any of embodiments 41-72, wherein the chemiluminescent-labeled specific binding partner comprises a chemiluminescent labeled compound connected to an analog of the analyte and further wherein the analyte and the chemiluminescent-labeled specific binding partner are adapted to compete to bind with the activator-labeled specific binding partner.

74. The kit of any of embodiments 41-73, wherein the unbound chemiluminescent substrate is selected from the group consisting of cyclic hydrazides such as luminol and isoluminol, imidazole compounds such as lophine, acridinium esters such as lucigenin and acridan, phthalhydrazides such as 2,3-dihydro-1,4-phthalazinedione, luciferin, and 1,2 dioxyetane containing compounds such as dione, 3-(2'-spiroadamantane)-4-methoxy-4-(3"-phosphoryloxy) phenyl-1,2-dioxetane (AMPPD), and, 3-(2'-spiroadamantane)-4-methoxy-4-(3"-beta-D'-galactopyrano-yloxy)phenyl-1,2-dioxetane (AMPGD), disodium 3-(4-methoxyspiro {1,2-dioxetane-3,2'-(5'-chloro)tricyclo[3.3.1.13,7]decan}-4-yl)phenyl phosphate, and 1,2-dioxetanedione, adamantylidene-adamantyl-1,2-dioxetane, particularly luminol or isoluminol, and more particularly luminol.

75. The kit of any of embodiments 41-74, wherein the unbound chemiluminescent substrate comprises luminol.

76. The kit of any of embodiments 41-75, wherein the wavelength of maximum luminescence intensity of the unbound chemiluminescent substrate is different from the wavelength of maximum luminescence intensity of the chemiluminescent label.

77. A solution phase assay method for an analyte in a sample, the solution phase assay method comprising:
a) forming an aqueous reaction mixture comprising the following components:
the sample,
a chemiluminescent-labeled specific binding partner comprising a chemiluminescent label compound connected directly or indirectly to a first specific binding partner, wherein the chemiluminescent label compound is a compound of the formula

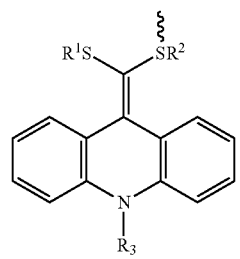

wherein
the wavy line designates the site of attachment to the specific binding partner or to a linker connecting the compound to the specific binding partner;
$R^1$, $R^2$, and $R^3$ are independently selected from substituted alkyl, unsubstituted alkyl, substituted alkyenyl, unsubstituted alkenyl, substituted alkynyl, unsubstituted alkynyl, substituted aralkyl, and unsubstituted aralky groups of 1-20 carbon atoms, wherein when $R^1$ or $R^2$ is substituted it is substituted with 1-3 substituents, each substituent independently selected from carbonyl, carboxyl, tri (C1-C8)alkylsilyl, $-SO_3^-$, $-OSO_3^{2-}$ glycosyl, $-PO_3^-$, $-OPO_3^{2-}$, halogen, hydroxyl, thiol, amino, $C(O)NHNH_2$, quaternary ammonium, and quaternary phosphonium,
an activator-labeled specific binding partner comprising an activator label compound having peroxidase activity connected directly or indirectly to a second specific binding partner, and
a selective signal inhibiting agent selected from the group consisting of L-ascorbic acid, 6-hydroxy-2,5,7,8-tetramethylchromane-2-carboxylic acid, 2-aminophenol, 3-amino-L-tyrosine, 4-chlorocatechol, phenoxazine, 2-bromobenzene-1,4, -diol, 5,6-isopropylidene ascorbic acid, and ascorbic acid 6-palmitate, by adding the components, in any order or concurrently, to an aqueous solution,
wherein all of the components are soluble in the aqueous solution and none of the components are immobilized to a solid support, and
wherein the chemiluminescent-labeled specific binding partner and the activator-labeled specific binding partner bind to the analyte present in the sample to form a binding complex in the aqueous solution; and
b) adding to the aqueous reaction mixture a trigger solution comprising a peroxide compound, wherein the trigger solution releases a detectable chemiluminescent signal in the presence of the selective signal inhibiting agent that is correlated to the amount of the analyte-bound chemiluminescent-labeled specific binding partner and the analyte-bound activator-labeled specific binding partner in the aqueous reaction mixture, and wherein the selective signal inhibiting agent causes the ratio of signal produced by reaction between the chemiluminescent label compound and the activator label compound to exceed the signal from reaction between the chemiluminescent label compound and the activator label compound when not in such a comples;
characterized in that
the reaction mixture further comprises an unbound chemiluminescent substrate that produces a detectable background signal that is not correlated to the concentration of the analyte in the sample.

78. A kit for detecting an analyte in a sample comprising:

a first specific binding partner for the analyte;

a chemiluminescent compound conjugated to the first specific binding partner;

a second specific binding partner for the analyte;

an activator compound conjugated to the second specific binding partner;

a selective signal inhibiting agent; and a trigger solution, wherein all of the foregoing components of the kit are soluble in aqueous solution, wherein the chemiluminescent compound is an acridan ketendithioacetal compound having the formula

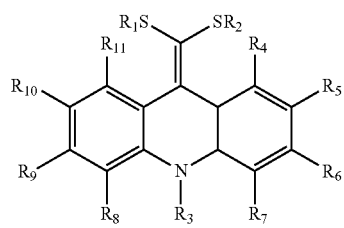

wherein each of $R_1$ and $R_2$ are selected from the group consisting of H, alkyl, substituted alkyl, alkenyl, substituted alkenyl, alkynyl, substituted alkynyl, aryl, substituted aryl, aralkyl, or substituted aralkyl. When $R_1$ and $R_2$ is substituted, it is most commonly substituted with 1-3 radicals selected from carbonyl, carboxyl, tri (alkyl) silyl, glycosyl, $-SO_3^-$, $-OSO_3^-$, $-PO_3^-$, $-OPO_3^-$, halogen, hydroxy, thiol, amino, quaternary ammonium, and quaternary phosphonium, $R_3$ is selected from the group consisting of H, alkyl, substituted alkyl, alkenyl, substituted alkenyl, alkynyl, substituted alkynyl, aryl, substituted aryl, aralkyl, or substituted aralkyl, each of $R_4$—$R_{11}$ is independently H, alkyl, substituted alkyl, alkenyl, substituted alkenyl, alkynyl, substituted alkynyl, aryl, substituted aryl, aralkyl, substituted aralkyl, alkoxy, aryloxy, halogen, amino, substituted amine, carboxyl, carboalkoxy, carboxyamide, cyano, or sulfonate, wherein pairs f proximal $R_4$—$R_{11}$ moieties-can be covalently bound to form a five to seven membered carbon ring or heterocyclic ring, wherein the selective signal inhibiting agent is selected from the group consisting of glutathione, ascorbic acid, particularly L-ascorbic acid, salts of ascorbic acid, particularly salts of L-ascorbic acid, uric acid, L-ascorbic acid-6-palmitate, tocopherol, 5,6-isopropylidene-L-acobic acid, isoascorbic acid, including D-isoascorbic acid, L-isoasocrbic acid, or both, sodium sulfite, diethylhydroxylamine, BHT,

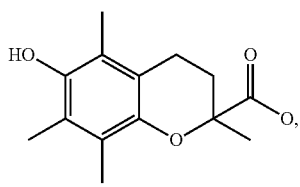

-continued

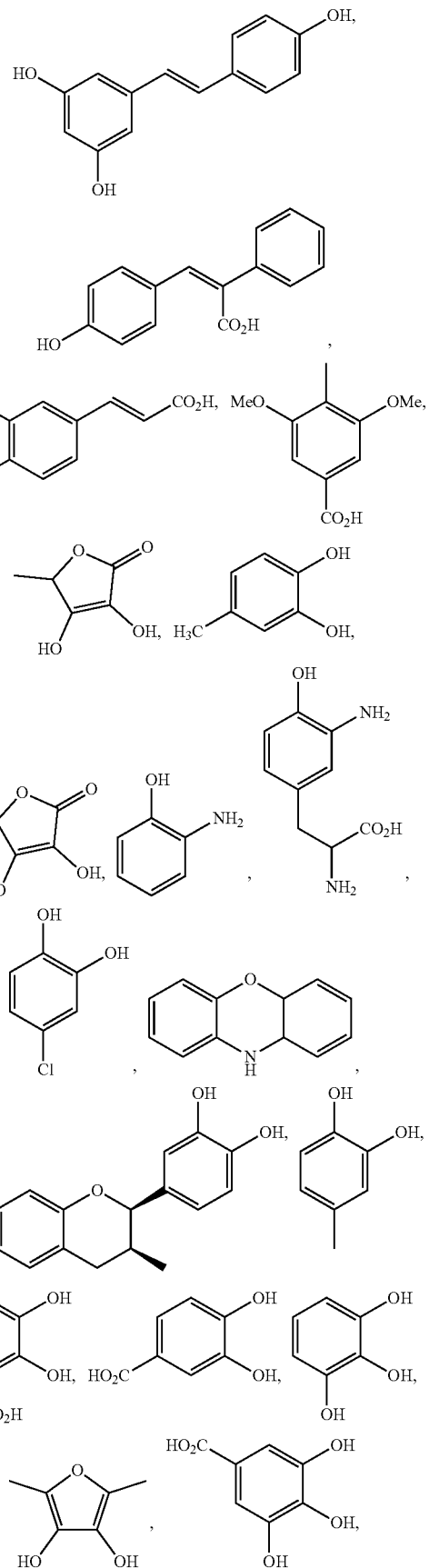

-continued

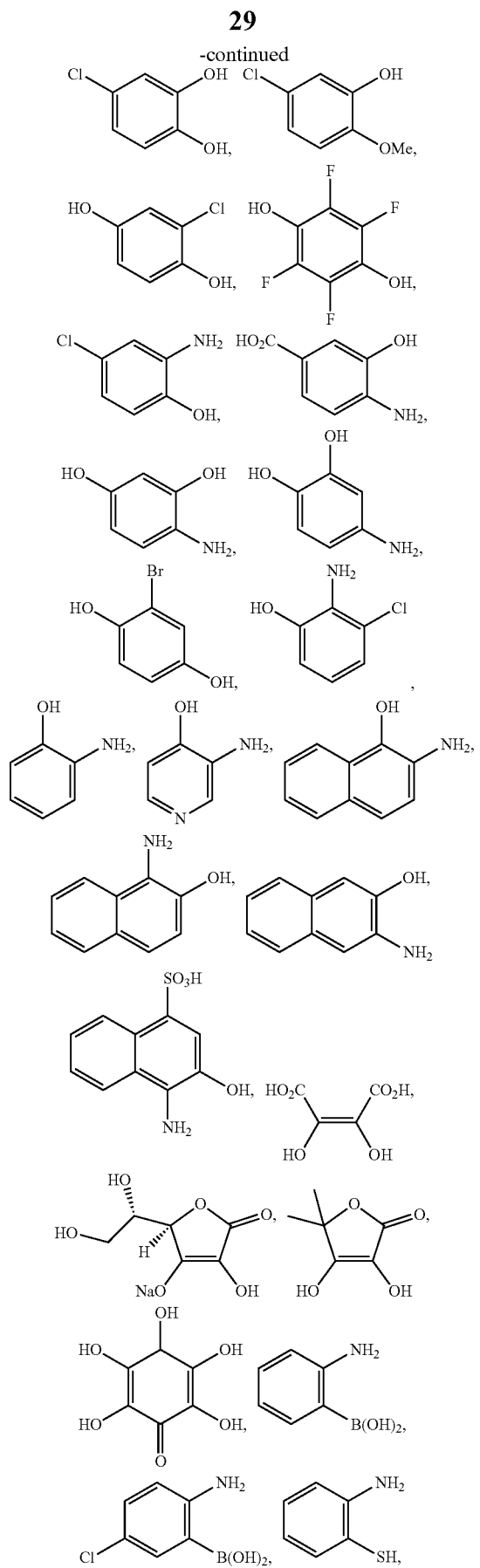

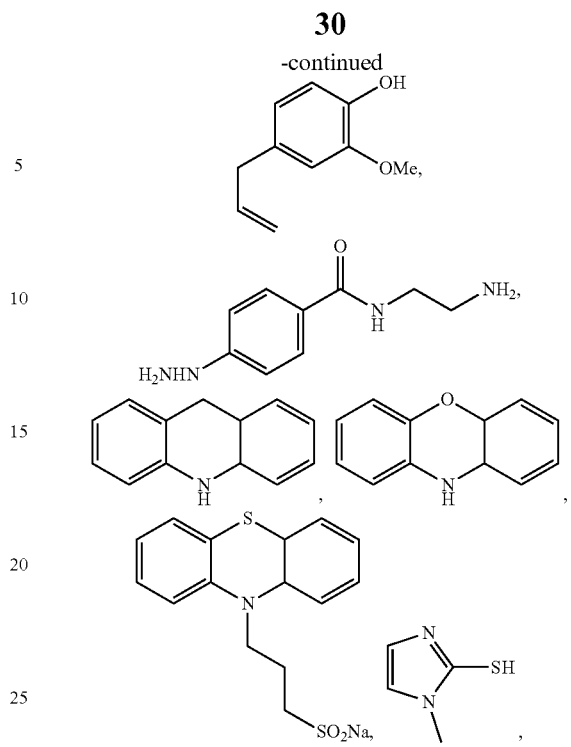

and combinations of the foregoing.

79. The kit of embodiment 78, wherein the chemiluminescent label compound is a compound of the formula

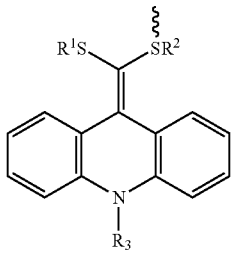

wherein
the wavy line designates the site of attachment to the specific binding partner or to a linker connecting the compound to the specific binding partner;
$R_1$, $R_2$, and $R_3$ are independently selected from substituted alkyl, unsubstituted alkyl, substituted alkyenyl, unsubstituted alkenyl, substituted alkynyl, unsubstituted alkynyl, substituted aralkyl, and unsubstituted aralky groups of 1-20 carbon atoms, wherein when $R^1$ or $R_2$ is substituted it is substituted with 1-3 substituents, each substituent independently selected from carbonyl, carboxyl, tri (C1-C8)alkylsilyl, —$SO_3^-$, —$OSO_3^{2-}$-glycosyl, —$PO_3^-$, —$OPO_3^{2-}$, halogen, hydroxyl, thiol, amino, C(O)NHNH$_2$, quaternary ammonium, and quaternary phosphonium.

EXAMPLES

Materials

Ethylenediaminetetraacetic acid dipotassium salt (EDTA-dipotassium salt), para-Coumaric acid, TWEEN 20, Tris base, Tris hydrochloride, Sodium ascorbate, and Lucigenin were obtained from the Sigma-Aldrich Corporation, St. Louis, MO.

Hydrogen peroxide (30%, BAKER analyzed) was obtained from VWR International, Radnor, PA.

Ethanol (200 proof) was obtained from Decon Labs Incorporated, King of Prussia, PA.

PVP360 [poly(vinylpyrrolidinone) with an average molecular weight of 360,000] and PEG-6000 [poly(ethyleneglycol) with an average molecular weight of 6000] were obtained from the Sigma-Aldrich Corporation.

Cow IgG SPARCL Assay kits were obtained from Life Diagnostics Incorporated, West Chester, PA.

Cow IgG standard solution was prepared in PBS according to the solution formulation described in Table 1.

Cow IgG standard+lucigenin solution was prepared by combining 20 parts by volume of the cow IgG standard solution (Table 1) with 1 part by volume of a saturated solution of lucigenin in deionized water.

The solution containing (anti-Cow IgG)-HRP conjugate was prepared according to the assay kit instructions.

The solution containing acridan-labeled anti-Cow IgG was prepared according to the assay kit instructions and additionally supplemented with sodium ascorbate (200 micromolar).

Horse serum (16050-130) and phosphate buffered saline (PBS) were obtained from Thermo Fisher Scientific Incorporated. Test samples with horse serum were prepared in PBS at dilution concentrations of 1e-1, 1e-2, 1e-3, 1e-4, and 1e-5 (volume/volume).

TABLE 1

Cow IgG standard solution

| Component | Concentration in the PBS Solution |
|---|---|
| Cow IgG standard (from SPARCL assay kit) | 50 ppb |
| TWEEN 20 | 3 wt. % |
| PVP360 | 3 wt. % |
| PEG-6000 | 3 wt. % |

The trigger solution for Example 1 was prepared as an aqueous solution of the components listed in Table 2.

TABLE 2

Trigger Solution Composition

| Component | Concentration in the Trigger Solution (g/L) |
|---|---|
| p-Coumaric acid | 1.31 |
| EDTA-dipotassium salt | 0.40 |
| TWEEN 20 | 2.00 |
| Hydrogen peroxide (30%) | 11.33 |
| Ethanol (200 proof) | 32.00 |
| Tris base | 1.33 |
| Tris hydrochloride | 2.22 |

Cortisol SPARCL Assay kits were obtained from Life Diagnostics Incorporated.

Cortisol standard solution was prepared using cortisol stock and diluent provided in the assay kit.

The solution containing cortisol-HRP conjugate was prepared by mixing cortisol-HRP conjugate from the kit (781 microliters) with 249 microliters of diluent from the kit.

The solution containing anti-cortisol acridan conjugate was prepared by mixing anti-cortisol acridan conjugate from the kit (2.5 microliters) with 247.5 microliters of diluent from the kit.

Calculations

The Scale Factor (SF) was determined dividing the reported Background Signal of the Standard Sample by the reported Background Signal of the Test Sample.

The Corrected Analyte Signal of the Test Sample was calculated by multiplying the Analyte Signal of the Test Sample by the Scale Factor (SF).

Example 1

Test samples were prepared in a reflective-white 96-well plate by first adding the horse serum dilution samples (20 microliters) to the wells in the plate. Each well contained a single test sample and each test sample was tested in triplicate. For wells containing the standard samples, 20 microliters of the PBS solution was used (3 replicates). Next, 20 microliters of the cow IgG standard+lucigenin solution was added to each well and the plate was shaken for 30 seconds at 300 rpm. Anti-cow IgG-HRP conjugate solution (20 microliters) was added to each well and the plate was shaken for 30 seconds at 300 rpm. Acridan-labeled anti-Cow IgG conjugate solution (20 microliters) was then added to each well and the plate was shaken for 30 seconds at 300 rpm. A 3M MLS II injecting luminometer (available from the 3M Corporation, Maplewood, MN) was used to added 30 microliters of trigger solution to each well. The instrument was set to simultaneously read and integrate the flash luminescence signal (Analyte Signal of either the Test Sample or the Standard Sample) for three seconds. After recording the flash luminescence signal (relative light units, RLU), the second luminescence signal (Background Signal of the Test Sample or Standard Sample) was recorded during the time period 60-70 seconds post injection (with one second integration times). The RLU value reported for the second signal was the average of the values recorded over the 10 second time range. In Tables 3-7, the Background Signal of Test Sample (RLU), Mean Background Signal of Standard Sample (RLU), Analyte Signal of Test Sample (RLU), Mean Analyte Signal of Standard Sample (RLU), calculated Scale Factor, and Corrected Analyte Signal of Test Sample (RLU) values are reported for each replicate sample. A determination as to whether the Corrected Analyte Signal for each Test Sample was within ±20% of the Analyte Signal for the corresponding Standard Sample is also reported in the Tables.

For the three wells containing the standard sample, the individual background signals were 643, 748, and 853 RLU. The Scale Factor was calculated using the mean value of 748 RLU for the Background Signal of Standard Sample (n=3). The Mean Analyte Signal of the Standard Sample (RLU) was calculated to be 38015 RLU (with the three individual standard sample analyte signals being 35903, 38075, and 40067 RLU).

TABLE 3

Determination of Corrected Analyte Signal of Test Sample (IgG) with 1e-5 Horse Serum as Added Interferent

| | Test Sample Replicates | | |
|---|---|---|---|
| | 1 | 2 | 3 |
| Background Signal of Test Sample (RLU) | 697 | 1066 | 1018 |
| Mean Background Signal of Standard Sample | 748 | 748 | 748 |
| Scale Factor | 1.07 | 0.70 | 0.73 |
| Analyte Signal of Test Sample (RLU) | 38645 | 59717 | 48375 |
| Mean Analyte Signal of Standard Sample (RLU) | 38015 | 38015 | 38015 |
| Corrected Analyte Signal of Test Sample (RLU) | 41350 | 41802 | 35314 |
| Corrected Analyte Signal of | Yes | Yes | Yes |

TABLE 3-continued

Determination of Corrected Analyte Signal of Test Sample (IgG) with 1e−5 Horse Serum as Added Interferent

|  | Test Sample Replicates | | |
| --- | --- | --- | --- |
|  | 1 | 2 | 3 |
| Test Sample is within ± 20% of Mean Analyte Signal of Standard Sample | | | |

TABLE 4

Determination of Corrected Analyte Signal of Test Sample (IgG) with 1e−5 Horse Serum as Added Interferent

|  | Test Sample Replicates | | |
| --- | --- | --- | --- |
|  | 1 | 2 | 3 |
| Background Signal of Test Sample (RLU) | 578 | 1106 | 881 |
| Mean Background Signal of Standard Sample | 748 | 748 | 748 |
| Scale Factor | 1.29 | 0.68 | 0.85 |
| Analyte Signal of Test Sample (RLU) | 26397 | 54250 | 39458 |
| Mean Analyte Signal of Standard Sample (RLU) | 38015 | 38015 | 38015 |
| Corrected Analyte Signal of Test Sample (RLU) | 34052 | 36890 | 33539 |
| Corrected Analyte Signal of Test Sample is within ± 20% of Mean Analyte Signal of Standard Sample | Yes | Yes | Yes |

TABLE 5

Determination of Corrected Analyte Signal of Test Sample (IgG) with 1e−3 Horse Serum as Added Interferent

|  | Test Sample Replicates | | |
| --- | --- | --- | --- |
|  | 1 | 2 | 3 |
| Background Signal of Test Sample (RLU) | 547 | 950 | 792 |
| Mean Background Signal of Standard Sample | 748 | 748 | 748 |
| Scale Factor | 1.37 | 0.79 | 0.94 |
| Analyte Signal of Test Sample (RLU) | 25661 | 51732 | 38585 |
| Mean Analyte Signal of Standard Sample (RLU) | 38015 | 38015 | 38015 |
| Corrected Analyte Signal of Test Sample (RLU) | 35156 | 40868 | 36270 |
| Corrected Analyte Signal of Test Sample is within ± 20% of Mean Analyte Signal of Standard Sample | Yes | Yes | Yes |

TABLE 6

Determination of Corrected Analyte Signal of Test Sample (IgG) with 1e−2 Horse Serum as Added Interferent

|  | Test Sample Replicates | | |
| --- | --- | --- | --- |
|  | 1 | 2 | 3 |
| Background Signal of Test Sample (RLU) | 283 | 790 | 616 |
| Mean Background Signal of Standard Sample | 748 | 748 | 748 |
| Scale Factor | 2.64 | 0.95 | 1.21 |
| Analyte Signal of Test Sample (RLU) | 14738 | 33775 | 25536 |
| Mean Analyte Signal of Standard Sample (RLU) | 38015 | 38015 | 38015 |
| Corrected Analyte Signal of Test Sample (RLU) | 39807 | 32086 | 30989 |
| Corrected Analyte Signal of Test Sample is within ± 20% of Mean Analyte Signal of Standard Sample | Yes | Yes | Yes |

TABLE 7

Determination of Corrected Analyte Signal of Test Sample (IgG) with 1e−1 Horse Serum as Added Interferent

|  | Test Sample Replicates | | |
| --- | --- | --- | --- |
|  | 1 | 2 | 3 |
| Background Signal of Test Sample (RLU) | 139 | 383 | 327 |
| Mean Background Signal of Standard Sample | 748 | 748 | 748 |
| Scale Factor | 5.38 | 1.95 | 2.29 |
| Analyte Signal of Test Sample (RLU) | 10707 | 15478 | 12754 |
| Mean Analyte Signal of Standard Sample (RLU) | 38015 | 38015 | 38015 |
| Corrected Analyte Signal of Test Sample (RLU) | 57602 | 30182 | 29206 |
| Corrected Analyte Signal of Test Sample is within ± 20% of Mean Analyte Signal of Standard Sample | No | No | No |

Comparative Example A

The same procedure as described in Example 2 was followed with the exception that the cow IgG standard+lucigenin solution (20 microliters) was replaced with the cow IgG standard solution (20 microliters). In Tables 8-12, the Analyte Signal of Test Sample (RLU) and the Mean Analyte Signal of Standard Sample (RLU) values are reported for each replicate sample. The Mean Analyte Signal of the Standard Sample (RLU) was calculated to be 37694 RLU (with the three individual standard sample analyte signals being 36955, 37062, and 39066 RLU). A determination as to whether the Analyte Signal for each Test Sample was within ±20% of the Analyte Signal for the corresponding Standard Sample is also reported in the Tables.

TABLE 8

Comparison of Analyte Signal of Test Sample and Analyte Signal of Standard Sample with 1e−5 Horse Serum as Added Interferent

|  | Test Sample Replicates | | |
| --- | --- | --- | --- |
|  | 1 | 2 | 3 |
| Analyte Signal of Test Sample (RLU) | 44823 | 52240 | 48061 |
| Mean Analyte Signal of Standard Sample (RLU) | 37694 | 37694 | 37694 |
| Corrected Analyte Signal of Test Sample is within ± 20% of Mean Analyte Signal of Standard Sample | Yes | No | No |

TABLE 9

Comparison of Analyte Signal of Test Sample and Analyte Signal of Standard Sample with 1e−4 Horse Serum as Added Interferent

|  | Test Sample Replicates | | |
| --- | --- | --- | --- |
|  | 1 | 2 | 3 |
| Analyte Signal of Test Sample (RLU) | 30610 | 47831 | 39052 |
| Mean Analyte Signal of Standard Sample (RLU) | 37694 | 37694 | 37694 |
| Corrected Analyte Signal of Test Sample is within ± 20% of Mean Analyte Signal of Standard Sample | Yes | No | Yes |

TABLE 10

Comparison of Analyte Signal of Test Sample and Analyte Signal of Standard Sample with 1e-3 Horse Serum as Added Interferent

|  | Test Sample Replicates | | |
|---|---|---|---|
|  | 1 | 2 | 3 |
| Analyte Signal of Test Sample (RLU) | 29907 | 45515 | 38403 |
| Mean Analyte Signal of Standard Sample (RLU) | 37694 | 37694 | 37694 |
| Corrected Analyte Signal of Test Sample is within ± 20% of Mean Analyte Signal of Standard Sample | No | No | Yes |

TABLE 11

Comparison of Analyte Signal of Test Sample and Analyte Signal of Standard Sample with 1e-2 Horse Serum as Added Interferent

|  | Test Sample Replicates | | |
|---|---|---|---|
|  | 1 | 2 | 3 |
| Analyte Signal of Test Sample (RLU) | 17124 | 29716 | 25446 |
| Mean Analyte Signal of Standard Sample (RLU) | 37694 | 37694 | 37694 |
| Corrected Analyte Signal of Test Sample is within ± 20% of Mean Analyte Signal of Standard Sample | No | No | No |

TABLE 12

Comparison of Analyte Signal of Test Sample and Analyte Signal of Standard Sample with 1e-1 Horse Serum as Added Interferent

|  | Test Sample Replicates | | |
|---|---|---|---|
|  | 1 | 2 | 3 |
| Analyte Signal of Test Sample (RLU) | 12452 | 13552 | 12768 |
| Mean Analyte Signal of Standard Sample (RLU) | 37694 | 37694 | 37694 |
| Corrected Analyte Signal of Test Sample is within ± 20% of Mean Analyte Signal of Standard Sample | No | No | No |

Comparative Example B

Test samples of horse serum (1e-1 to 1e-5 dilutions) were prepared as described above. The standard samples were PBS solution with no horse serum added. Test samples and standard samples were analyzed using a Cow IgG ELISA kit (catalog number IGG-11, obtained from Life Diagnostics Incorporated) according to the manufacturer's directions. The absorbance value (A450) for each well was determined with a BioTek POWERWAVE 340 plate reader (obtained from Bio Tek Instruments Incorporated, Winooski, VT). The absorbance (A450) value for each replicate (Test and Standard Samples) is reported in Table 13. and compared to the mean A450 value calculated for the Standard Samples. The mean A450 value for the three standard samples was 0.551.

TABLE 13

|  | Horse Serum Concentration | Absorbance (A450) | Calculated Percentage of the mean Standard Sample Absorbance (A450) | Within 20% of Standard Sample |
|---|---|---|---|---|
| Standard Sample | 0 | 0.555 | 101 | NA |
| Standard Sample | 0 | 0.532 | 97 | NA |
| Standard Sample | 0 | 0.565 | 103 | NA |
| Test Sample | 1e-5 | 0.600 | 109 | Yes |
| Test Sample | 1e-5 | 0.584 | 106 | Yes |
| Test Sample | 1e-5 | 0.567 | 103 | Yes |
| Test Sample | 1e-4 | 0.523 | 95 | Yes |
| Test Sample | 1e-4 | 0.589 | 107 | Yes |
| Test Sample | 1e-4 | 0.606 | 110 | Yes |
| Test Sample | 1e-3 | 0.501 | 91 | Yes |
| Test Sample | 1e-3 | 0.626 | 114 | Yes |
| Test Sample | 1e-3 | 0.589 | 107 | Yes |
| Test Sample | 1e-2 | 0.490 | 89 | Yes |
| Test Sample | 1e-2 | 0.501 | 91 | Yes |
| Test Sample | 1e-2 | 0.490 | 89 | Yes |
| Test Sample | 1e-1 | 0.180 | 33 | No |
| Test Sample | 1e-1 | 0.186 | 34 | No |
| Test Sample | 1e-1 | 0.196 | 36 | No |

Example 2

Dry feed corn was ground using a Romer Series II mill (Romer Labs, Getzerdorf, Austria) and passed through a #20 sieve. The sieved corn (2 g) was added to 8 mL of the buffer from a Cortisol SPARCL Assay kit (obtained from Life Diagnostics Incorporated). The resulting slurry was mixed by repeated inversion for 3 minutes. The supernatant from the sample was filtered through a 0.45 micron syringe filter (Thermo Fischer Scientific, Waltham MA USA). Five dilution series of the filtrate were prepared using buffer from the assay kit. (2×, 4×, 6×, 8×, and 10×). For the undiluted sample and each dilution series, eight individual test samples were prepared. Each test sample was spiked with a different concentration of cortisol (25 nM, 12.5 nM, 6.25 nM, 3.13 nM, 1.56 nM, 0.78 nM, 0.39 nM, or 0.20 nM). A corresponding series of standard samples was prepared from the cortisol solution standard. Lucigenin (5 microliters of a 10 mg/mL aqueous solution) was added to each sample (test and standard samples).

For the competitive format assay, samples were prepared in the 96-well plate supplied in the kit by first adding the cortisol spiked samples (50 microliters) to the wells in the plate. Each well contained a single test or standard sample. Next, 25 microliters of the cortisol-HRP conjugate solution was added to each well and the plate was shaken for 30 seconds at 300 rpm. Anti-cortisol-acridan conjugate solution (25 microliters) was then added to each well and the plate shaken for 30 seconds at 300 rpm.

A Turner BioSystems TD 20/20n luminometer (Promega Corporation, Madison, WI) was used to add 30 microliters of trigger solution (obtained from the assay kit) to each well of the assay plate. The instrument was set to simultaneously read and integrate the luminescence signal for sixty seconds (0.1 second integration time). The Analyte Signal (of either the Test Sample or the Standard Sample) was measured during the first 20 seconds and averaged. After recording the flash luminescence signal, the second luminescence signal (Background Signal of the Test Sample or Standard Sample) was recorded during the time period of seconds 58 and 59 and averaged.

In Tables 14-19, the Background Signal of Test Sample (RLU), Background Signal of Standard Sample (RLU), Analyte Signal of Test Sample (RLU), Analyte Signal of Standard Sample (RLU), calculated Scale Factor, and Corrected Analyte Signal of Test Sample (RLU) values are reported for each sample.

A determination as to whether the Corrected Analyte Signal for each Test Sample was within +7.5% of the Analyte Signal for the corresponding Standard Sample is reported in Table 26.

TABLE 14

Determination of Corrected Analyte Signal (RLU) of Test Sample (Cortisol) with 10x Diluted Corn Extract as Interferent

| | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| Background Signal Test Sample (RLU) | 553317 | 658535 | 543582 | 490741 | 578933 | 328499 | 338088 | 271638 |
| Background Signal Standard Sample | 536908 | 574839 | 526961 | 497374 | 538676 | 411997 | 412127 | 375979 |
| Scale Factor | 0.970 | 0.873 | 0.970 | 1.014 | 0.930 | 1.254 | 1.219 | 1.384 |
| Analyte Signal Test Sample (RLU) | 3236225 | 3613034 | 3237134 | 2671864 | 2457679 | 1296061 | 934213 | 463894 |
| Analyte Signal Standard Sample (RLU) | 3154464 | 3121706 | 3106978 | 2738340 | 2252914 | 1583308 | 1163059 | 645372 |
| Corrected Analyte Signal Test Sample (RLU) | 3140250 | 3153836 | 3138441 | 2707979 | 2286782 | 1625496 | 113880 | 642086 |

TABLE 15

Determination of Corrected Analyte Signal (RLU) of Test Sample (Cortisol) with 8x Diluted Corn Extract as Interferent

| | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| Background Signal Test Sample (RLU) | 566466 | 625861 | 536361 | 486262 | 571577 | 321871 | 335035 | 268353 |
| Background Signal Standard Sample | 536908 | 574839 | 526961 | 497374 | 538676 | 411997 | 412127 | 375979 |

TABLE 15-continued

Determination of Corrected Analyte Signal (RLU) of Test Sample (Cortisol) with 8x Diluted Corn Extract as Interferent

| | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| Scale Factor | 0.948 | 0.918 | 0.982 | 1.023 | 0.942 | 1.280 | 1.230 | 1.401 |
| Analyte Signal Test Sample (RLU) | 3329442 | 3318155 | 3099781 | 2717973 | 2343828 | 1214894 | 950182 | 463151 |
| Analyte Signal Standard Sample (RLU) | 3154464 | 3121706 | 3106978 | 2738340 | 2252914 | 1583308 | 1163059 | 645372 |
| Corrected Analyte Signal Test Sample (RLU) | 3155821 | 3047647 | 3045454 | 2780087 | 2208913 | 1555075 | 1168820 | 648902 |

TABLE 16

Determination of Corrected Analyte Signal (RLU) of Test Sample (Cortisol) with 6x Diluted Corn Extract as Interferent

| | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| Background Signal Test Sample (RLU) | 506331 | 592650 | 491769 | 446645 | 523492 | 300334 | 297698 | 256791 |
| Background Signal Standard Sample | 536908 | 574839 | 526961 | 497374 | 538676 | 411997 | 412127 | 375979 |
| Scale Factor | 1.060 | 0.970 | 1.072 | 1.114 | 1.029 | 1.372 | 1.384 | 1.464 |
| Analyte Signal Test Sample (RLU) | 2768949 | 3050402 | 2815308 | 2343694 | 2054745 | 1131264 | 787353 | 431397 |
| Analyte Signal Standard Sample (RLU) | 3154464 | 3121706 | 3106978 | 2738340 | 2252914 | 1583308 | 1163059 | 645372 |
| Corrected Analyte Signal Test Sample (RLU) | 2936167 | 2958729 | 3016776 | 2609887 | 2114342 | 1551863 | 1089996 | 631627 |

TABLE 17

Determination of Corrected Analyte Signal (RLU) of Test Sample (Cortisol) with 4x Diluted Corn Extract as Interferent

| | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| Background Signal Test Sample (RLU) | 515612 | 504591 | 478380 | 408393 | 464877 | 281948 | 263326 | 216780 |
| Background Signal Standard Sample | 536908 | 574839 | 526961 | 497374 | 538676 | 411997 | 412127 | 375979 |
| Scale Factor | 1.041 | 1.139 | 1.102 | 1.218 | 1.159 | 1.461 | 1.565 | 1.734 |
| Analyte Signal Test Sample (RLU) | 3178009 | 2874138 | 2961188 | 2337276 | 1854375 | 963160 | 544177 | 302927 |
| Analyte Signal Standard Sample (RLU) | 3154464 | 3121706 | 3106978 | 2738340 | 2252914 | 1583308 | 1163059 | 645372 |

TABLE 17-continued

Determination of Corrected Analyte Signal (RLU) of Test Sample (Cortisol) with 4x Diluted Corn Extract as Interferent

| | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| Corrected Analyte Signal Test Sample (RLU) | 3309268 | 3274268 | 3261908 | 2846526 | 2148757 | 1407418 | 851682 | 525392 |

TABLE 18

Determination of Corrected Analyte Signal (RLU) of Test Sample (Cortisol) with 2x Diluted Corn Extract as Interferent

| | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| Background Signal Test Sample (RLU) | 444728 | 405951 | 389423 | 314420 | 370965 | 206136 | 191641 | 149302 |
| Background Signal Standard Sample | 536908 | 574839 | 526961 | 497374 | 538676 | 411997 | 412127 | 375979 |
| Scale Factor | 1.207 | 1.416 | 1.353 | 1.582 | 1.452 | 1.999 | 2.151 | 2.518 |
| Analyte Signal Test Sample (RLU) | 2839788 | 2322543 | 2305990 | 1448249 | 1152668 | 452434 | 231905 | 138338 |
| Analyte Signal Standard Sample (RLU) | 3154464 | 3121706 | 3106978 | 2738340 | 2252914 | 1583308 | 1163059 | 645372 |
| Corrected Analyte Signal Test Sample (RLU) | 3428397 | 3288790 | 3120429 | 2290953 | 1673780 | 90262 | 498716 | 348368 |

TABLE 19

Determination of Corrected Analyte Signal (RLU) of Test Sample (Cortisol) with Undiluted Corn Extract as Interferent

| | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| Background Signal Test Sample (RLU) | 289665 | 329783 | 280283 | 223769 | 246972 | 166864 | 141918 | 99695 |
| Background Signal Standard Sample | 536908 | 574839 | 526961 | 497374 | 538676 | 411997 | 412127 | 375979 |
| Scale Factor | 1.854 | 1.743 | 1.880 | 2.223 | 2.181 | 2.469 | 2.904 | 3.771 |
| Analyte Signal Test Sample (RLU) | 1765315 | 1896647 | 1260152 | 737566 | 504160 | 30913 | 149433 | 73662 |
| Analyte Signal Standard Sample (RLU) | 3154464 | 3121706 | 3106978 | 2738340 | 2252914 | 1583308 | 1163059 | 645372 |
| Corrected Analyte Signal Test Sample (RLU) | 3272093 | 3306015 | 2369216 | 1639399 | 1099636 | 750382 | 433949 | 277801 |

Comparative Example C

The same procedure as described in Example 2 was followed with the exception that lucigenin was not added to any of the test samples. In Tables 20-25, the Analyte Signal of Test Sample (RLU) and the Analyte Signal of Standard Sample (RLU) values are reported for each sample. A determination as to whether the Analyte Signal for each Test Sample was within ±7.5% of the Analyte Signal for the corresponding Standard Sample is reported in Table 27.

TABLE 20

Comparison of Analyte Signal of Test Sample (Cortisol) and Analyte Signal of Standard Sample (Cortisol) with 10x Diluted Corn Extract as Interferent

| | Cortisol Concentration (nM) | | | | | | | |
| --- | --- | --- | --- | --- | --- | --- | --- | --- |
| | 0.20 | 0.39 | 0.78 | 1.56 | 3.13 | 6.25 | 12.5 | 25 |
| Analyte Signal Test Sample (RLU) | 2986836 | 2999758 | 2985115 | 2575683 | 2175063 | 1546084 | 1083165 | 610717 |
| Analyte Signal Standard Sample (RLU) | 3154464 | 3121706 | 3106978 | 2738340 | 2252914 | 1583308 | 1163059 | 645372 |

TABLE 21

Comparison of Analyte Signal of Test Sample (Cortisol) and Analyte Signal of Standard Sample (Cortisol) with 8x Diluted Corn Extract as Interferent

| | Cortisol Concentration (nM) | | | | | | | |
| --- | --- | --- | --- | --- | --- | --- | --- | --- |
| | 0.20 | 0.39 | 0.78 | 1.56 | 3.13 | 6.25 | 12.5 | 25 |
| Analyte Signal Test Sample (RLU) | 2961849 | 2860324 | 2858265 | 2609209 | 2073142 | 1459492 | 1096979 | 609017 |
| Analyte Signal Standard Sample (RLU) | 3154464 | 3121706 | 3106978 | 2738340 | 2252914 | 1583308 | 1163059 | 645372 |

TABLE 22

Comparison of Analyte Signal of Test Sample (Cortisol) and Analyte Signal of Standard Sample (Cortisol) with 6x Diluted Corn Extract as Interferent

| | Cortisol Concentration (nM) | | | | | | | |
| --- | --- | --- | --- | --- | --- | --- | --- | --- |
| | 0.20 | 0.39 | 0.78 | 1.56 | 3.13 | 6.25 | 12.5 | 25 |
| Analyte Signal Test Sample (RLU) | 2679541 | 2700131 | 2753105 | 2381779 | 1929545 | 1416228 | 994729 | 576422 |
| Analyte Signal Standard Sample (RLU) | 3154464 | 3121706 | 3106978 | 2738340 | 2252914 | 1583308 | 1163059 | 645372 |

TABLE 23

Comparison of Analyte Signal of Test Sample (Cortisol) and Analyte Signal of Standard Sample (Cortisol) with 4x Diluted Corn Extract as Interferent

| | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| Analyte Signal Test Sample (RLU) | 2618417 | 2590723 | 2580944 | 2252278 | 1700177 | 1113602 | 673883 | 415710 |
| Analyte Signal Standard Sample (RLU) | 3154464 | 3121706 | 3106978 | 2738340 | 2252914 | 1583308 | 1163059 | 645372 |

TABLE 24

Comparison of Analyte Signal of Test Sample (Cortisol) and Analyte Signal of Standard Sample (Cortisol) with 2x Diluted Corn Extract as Interferent

| | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| Analyte Signal Test Sample (RLU) | 2124224 | 2037724 | 1933408 | 1419467 | 1037069 | 560278 | 309003 | 215848 |
| Analyte Signal Standard Sample (RLU) | 3154464 | 3121706 | 3106978 | 2738340 | 2252914 | 1583308 | 1163059 | 645372 |

TABLE 25

Comparison of Analyte Signal of Test Sample (Cortisol) and Analyte Signal of Standard Sample (Cortisol) with Undiluted Corn Extract as Interferent

| | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| Analyte Signal Test Sample (RLU) | 1459352 | 1474481 | 1056669 | 731171 | 490437 | 334670 | 193541 | 123899 |
| Analyte Signal Standard Sample (RLU) | 3154464 | 3121706 | 3106978 | 2738340 | 2252914 | 1583308 | 1163059 | 645372 |

TABLE 26

Example 2 Results

Example 2: Corrected Analyte Signal of Test Sample is within +7.5% of Analyte Signal of Standard Sample

| Corn Extract (Added Interferent) Dilution Level | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| 10x | Yes | Yes | Yes | Yes | Yes | Yes | Yes | Yes |
| 8x | Yes | Yes | Yes | Yes | Yes | Yes | Yes | Yes |
| 6x | Yes | Yes | Yes | Yes | Yes | Yes | Yes | Yes |
| 4x | Yes | Yes | Yes | Yes | Yes | No | No | No |
| 2x | Yes | Yes | Yes | No | No | No | No | No |
| Undiluted | Yes | Yes | No | No | No | No | No | No |

TABLE 27

Comparative Example C Results

Comparative Example C: Analyte Signal of Test Sample is within +7.5% of Analyte Signal of Standard Sample

| Corn Extract (Added Interferent) Dilution Level | Cortisol Concentration (nM) | | | | | | | |
|---|---|---|---|---|---|---|---|---|
| | 0.20 | 0.39 | 0.78 | 1.56 | 3.13 | 6.25 | 12.5 | 25 |
| 10x | Yes | Yes | Yes | Yes | Yes | Yes | Yes | Yes |
| 8x | Yes | Yes | Yes | Yes | Yes | Yes | Yes | Yes |
| 6x | No | No | No | No | No | No | No | No |
| 4x | No | No | No | No | No | No | No | No |
| 2x | No | No | No | No | No | No | No | No |
| Undiluted | No | No | No | No | No | No | No | No |

Example 3

The effect of lucigenin, an unbound chemiluminescent substrate, on a solution phase luminescence assay was evaluated. A Cortisol SPARCL Assay (Life Diagnostics Incorporated) was used in the competitive format. Four different Samples A-D were prepared. In sample A, a cortisol standard sample (50 microliters) was prepared with a cortisol concentration of 25 nM using diluent from the assay kit. In sample B, a control standard (50 microliters) was prepared that did not contain cortisol (i.e contained only the diluent of Sample A). In sample C, 50 microliters of a cortisol standard sample was prepared as for Sample A and supplemented with 5 microliters of a 10 mg/mL aqueous solution of lucigenin. In Sample D, 50 microliters of a control standard sample was prepared as for Sample B and supplemented with 5 microliters of a 10 mg/mL aqueous solution of lucigenin. Samples A-D (50 microliters each) were individually analyzed according to the manufacturer's instructions provided with the assay kit. A Turner BioSystems TD 20/20n luminometer (Promega Corporation, Madison, WI) was used to add trigger solution (100 µL) o each well of the assay plate. The instrument was set to read the luminescence signal at the time points of 1, 2, 5, 10, 15, 20, 30, 40, and 60 seconds post addition of the trigger solution. Each reported luminescence value (RLU) was recorded as the average of the preceding ten 0.1 second integrations. The results are reported in Table 28.

TABLE 28

| | Luminescence Signal (RLU) | | | |
|---|---|---|---|---|
| Time (seconds) | Sample A Cortisol (25 nM) without Lucigenin | Sample B without Cortisol and without Lucigenin | Sample C Cortisol (25 nM) with Lucigenin | Sample D without Cortisol and with Lucigenin |
| 1 | 24695 | 500204 | 32773 | 281669 |
| 2 | 21928 | 325489 | 33014 | 195379 |
| 5 | 18750 | 163249 | 31739 | 115147 |
| 10 | 15393 | 96082 | 29732 | 80490 |
| 15 | 13731 | 69826 | 28939 | 65280 |
| 20 | 11968 | 56769 | 27976 | 57212 |
| 30 | 10106 | 39712 | 27384 | 47221 |
| 40 | 9144 | 31608 | 25668 | 43119 |
| 50 | 8163 | 26621 | 25408 | 38848 |
| 60 | 7673 | 22630 | 25097 | 35654 |

The invention claimed is:

1. A kit for assaying for an analyte, said kit comprising:
a first chemiluminescent compound, wherein said first chemiluminescent compound is an unbound chemiluminescent substrate;
a chemiluminescent-labeled specific binding partner comprising a second chemiluminescent compound, wherein the second chemiluminescent compound is a chemiluminescent label irreversibly bound to a first specific binding partner, the chemiluminescent-labeled specific binding partner being capable of binding configured to bind to the analyte to form an analyte-bound chemiluminescent labeled specific binding complex,
an activator-labeled specific binding partner comprising an activator label irreversibly bound to a second specific binding partner, and
a selective signal inhibiting agent; and
a trigger solution capable of producing configured to produce a background signal from the unbound chemiluminescent substrate and, in the presence of analyte, producing a detectable analyte signal correlated to an amount of analyte in a sample.

2. The kit of claim 1, wherein the trigger solution further comprises an enhancer selected from phenol compounds, aromatic amines, benzoxazoles, hydroxybenzothiazoles, aryl boronic acids, and mixtures of any of the foregoing.

3. The kit of claim 1, wherein the unbound chemiluminescent substrate is selected from a group consisting of luminol, isoluminol, lophine, acridinium esters such as lucigenin and acridan, phthalhydrazides such as 2,3-dihydro-1,4-phthalazinedione, luciferin, and 1,2 dioxyetane containing compounds such as dione, 3-(2'-spiroadamantane)-4-methoxy-4-(3"-phosphoryloxy)phenyl-1,2-dioxetane (AMPPD), and, 3-(2'-spiroadamantane)-4-methoxy-4-(3"-beta-D'-galactopyrano-yloxy)phenyl-1,2-dioxetane (AMPGD), disodium 3-(4-methoxyspiro {1,2-dioxetane-3,2'-(5'-chloro)tricyclo[3.3.1.13,7]decan}-4-yl)phenyl phosphate, and 1,2-dioxetanedione, adamantylidene-adamantyl-1,2-dioxetane, particularly luminol or isoluminol, and more particularly luminol.

4. The kit of claim 1, wherein said unbound chemiluminescent substrate comprises luminol.

5. The kit of claim 1, wherein the wavelength of maximum luminescence intensity of the unbound chemiluminescent substrate is different from the wavelength of maximum luminescence intensity of the chemiluminescent label.

* * * * *